US012797340B2

(12) United States Patent
Zhao

(10) Patent No.: US 12,797,340 B2
(45) **Date of Patent: *Nov. 17, 2026**

(54) CATIONIC POLYMER-FORMULATED NANOPARTICLES AND METHODS OF USE

(71) Applicant: Ann and Robert H. Lurie Children's Hospital of Chicago, Chicago, IL (US)

(72) Inventor: Youyang Zhao, Deerfield, IL (US)

(73) Assignee: Ann & Robert H. Lurie Children's Hospital of Chicago, Chicago, IL (US)

( * ) Notice: Subject to any disclaimer, the term of this patent is extended or adjusted under 35 U.S.C. 154(b) by 294 days.

This patent is subject to a terminal disclaimer.

(21) Appl. No.: 18/547,669

(22) PCT Filed: Feb. 23, 2022

(86) PCT No.: PCT/US2022/017501

§ 371 (c)(1),
(2) Date: Aug. 23, 2023

(87) PCT Pub. No.: WO2022/182745

PCT Pub. Date: Sep. 1, 2022

(65) Prior Publication Data

US 2024/0122866 A1 Apr. 18, 2024

Related U.S. Application Data

(60) Provisional application No. 63/152,815, filed on Feb. 23, 2021.

(51) Int. Cl.
*A61K 9/51* (2006.01)
*A61K 45/06* (2006.01)

(52) U.S. Cl.
CPC ........... *A61K 9/5153* (2013.01); *A61K 45/06* (2013.01)

(58) Field of Classification Search
None
See application file for complete search history.

(56) References Cited

U.S. PATENT DOCUMENTS 8,697,359 B1 4/2014 Zhang
8,795,965 B2 8/2014 Zhang
(Continued)

FOREIGN PATENT DOCUMENTS

WO WO-2018112470 A1 * 6/2018 ........... C12N 15/113
WO WO-2018227231 A1 * 12/2018 ........... A61K 9/0019
WO WO-2020077178 A1 * 4/2020 ......... A61K 47/6937

OTHER PUBLICATIONS

Logan W. Warriner, Joseph R. Duke III, Daniel W. Pack, and Jason E. DeRouchey. "Succinylated Polyethylenimine Derivatives Greatly Enhance Polyplex Serum Stability and Gene Delivery In Vitro." Biomacromolecules, vol. 19, 2018, pp. 4348-4357 and supplemental pp. 1-6. (Year: 2018).*
(Continued)

*Primary Examiner* — Isaac Shomer
(74) *Attorney, Agent, or Firm* — Quarles & Brady LLP

(57) ABSTRACT

Disclosed herein is a composition comprising a nanoparticle which comprises polyethylene glycol (PEG)-b-poly (D,L-lactide) (PLA) (PEG-b-PLA) co-polymer formulated with polyethylenimine (PEI) or other cationic polymers and one or more cargo molecules associated with the nanoparticle such as nucleic acids. Also provided are methods for delivering a cargo molecule to a cell in vitro and in vivo using the disclosed compositions.

20 Claims, 29 Drawing Sheets

Specification includes a Sequence Listing.

(56) References Cited

U.S. PATENT DOCUMENTS

| | | | | |
|---|---|---|---|---|
| 9,322,037 | B2 | 4/2016 | Liu et al. | |
| 2015/0147270 | A1* | 5/2015 | Merlin | A61K 47/6835 424/9.1 |
| 2018/0311177 | A1 | 11/2018 | Song et al. | |
| 2019/0133962 | A1* | 5/2019 | Saltzman | A61K 31/427 |
| 2021/0388393 | A1* | 12/2021 | Zhao | A61K 47/6937 |

OTHER PUBLICATIONS

Wei Dong, Guang-Hui Jin, Shu-Feng Li, Qi-Ming Sun, Ding-Yuan Ma, and Zi-Chun Hua. "Cross-linked Polyethylenimine as Potential DNA Vector for Gene Delivery with High Efficiency and Low Cytotoxicity." Acta Biochimica et Biophysica Sinica, vol. 38(11), 2006, pp. 780-787. (Year: 2006).*

Anna Calarco et al. "The genotoxicity of PEI-based nanoparticles is reduced by acetylation of polyethylenimine amines in human primary cells." Toxicology Letters, vol. 218, 2013, pp. 10-17. (Year: 2013).*

M.M. Mady et al. "Effect of Polymer Molecular Weight on the DNA/PEI Polyplexes Properties." Romanian Journal of Biophysics, vol. 21 No. 2, 2011, pp. 151-165. (Year: 2011) (Year: 2011).*

Hu-Lin Jiang et al. "Degradable Polyethylenimine-Based Gene Carriers for Cancer Therapy." Topics in Current Chemistry (Z), vol. 375:34, 2017, pp. 1-36. (Year: 2017).*

Shijian Ge et al. "Heteroaggregation between PEI-Coated Magnetic Nanoparticles and Algae: Effect of Particle Size on Algal Harvesting Efficiency." ACS Applied Materials & Interfaces, vol. 7, 2015, pp. 6102-6108 and S1-S16. (Year: 2015).*

Taehoon Sim et al. "Development of a gene carrier using a triblock co-polyelectrolyte with poly(ethylene imine)-poly(lactic acid)-poly (ethylene glycol)." Journal of Bioactive and Compatible Polymers, vol. 32(3), 2017, pp. 280-292. (Year: 2017).*

Uday K. Sukumar et al. "SP94-Targeted Triblock Copolymer Nanoparticle Delivers Thymidine Kinase-p53-Nitroreductase Triple Therapeutic Gene and Restores Anticancer Function against Hepatocellular Carcinoma in Vivo." ACS Applied Materials & Interfaces, vol. 12, 2020, pp. 11307-11319. (Year: 2020).*

Agrawal, et al., RNA interference: biology, mechanism, and applications, Microbiol. Mol. Biol. Rev., 67: 657-685 (2003).

Akbarzadeh et al., Liposome: classification, preparation, and applications, Nanoscale Res. Lett., 8: 102 (2013).

Anzalone et al., Search-and-replace genome editing without double-strand breaks or donor DNA, Nature, 576: 149-157 (2019).

Bartel D.P., MicroRNAs: target recognition and regulatory functions, Cell, 136 (2): 215-233 (2009).

Bhaya et al., CRISPR-Cas systems in bacteria and archaea: versatile small RNAs for adaptive defense and regulation, Annu. Rev. Genet., 45, 273 (2011).

Boussif et al., A versatile vector for gene and oligonucleotide transfer into cells in culture and in vivo: polyethylenimine, Proc. Natl. Acad. Sci. U.S.A.; 92: 7297-7301 (1995).

Breunig et al., Breaking up the correlation between efficacy and toxicity for nonviral gene delivery, Proc Natl Acad Sci USA, 104: 14454-14459 (2007).

Carroll et al., A mouse model for adult cardiac-specific gene deletion with CRISPR/Cas9, Proc Natl Acad Sci U S A 113, 338-343 (2016).

Chan et al., In: Cancer Nanotechnology; Grobmyer SR, Moudgil BM, editors. vol. 624. Humana Press; 2010. pp. 163-175.

Chuang et al., Lipid-based nanoparticles as a potential delivery approach in the treatment of rheumatoid arthritis, Nanomaterials, 8: 42 (2018).

Cines et al., Endothelial cells in physiology and in the pathophysiology of vascular disorders, Blood 91, 3527-3561 (1998).

Cong et al., Multiplex genome engineering using CRISPR/Cas systems, Science 339, 819-823 (2013).

Cox et al., Therapeutic genome editing: prospects and challenges, Nat Med 21, 121-131 (2015).

Dai et al., Identification of Synthetic Endothelial Cell-Specific Promoters by Use of a High-Throughput Screen, J. Virol., 78(12): 6209-6221 (2004).

Dana et al., Molecular mechanisms and biological functions of siRNA, International Journal of Biomedical Science, 13 (2):48-57 (2017).

Deveau et al., CRISPR/Cas system and its role in phage-bacteria interactions, Annu. Rev. Microbiol., 64: 475 (2010).

Devulapally R, Paulmurugan R., "Polymer nanoparticles for drug and small silencing RNA delivery to treat cancers of different phenotypes," Wiley Interdisciplinary Reviews. Nanomedicine and Nanobiotechnology. 2014;6(1).

Dinarvand et al., Polylactide-co-glycolide nanoparticles for controlled delivery of anticancer agents, International Journal of Nanomedicine, 6: 877-895 (2011).

Doudna et al., The new frontier of genome engineering with CRISPR-Cas9, Science, 346: 1258096 (2014).

Elbakry et al., Layer-by-layer assembled gold nanoparticles for siRNA delivery, Nano Lett., 9: 2059-2064 (2009).

Fabian et al., Regulation of mRNA translation and stability by microRNAs, Annual Review of Biochemistry, 79: 351-79 (2010).

Fadel et al., Functional analysis of the endothelial cell-specific Tie2/Tek promoter identifies unique protein-binding elements, Biochem J., 330 (Pt 1): 335-43 (1998).

Fuller et al., Intracellular delivery of core-shell fluorescent silica nanoparticles, Biomaterials, 29: 1526-1532 (2008).

Gao et al., miRNA oligonucleotide and sponge for miRNA-21 inhibition mediated by PEI-PLL in breast cancer therapy, Acta Biomater, 25: 184-193 (2015).

Garneau et al., The CRISPR/Cas bacterial immune system cleaves bacteriophage and plasmid DNA, Nature, 468: 67 (2010).

Gasiunas et al., Cas9-crRNA ribonucleoprotein complex mediates specific DNA cleavage for adaptive immunity in bacteria, Proc. Natl. Acad. Sci. U.S.A., 109, E2579 (2012).

Gaspar et al., Minicircle DNA vectors for gene therapy: advances and applications, Expert Opin Biol Ther., 15 (3):353-79 (2015).

Clement, et al., CRISPResso2 provides accurate and rapid genome editing sequence analysis. Nature Biotechnology, 37: 224-226 (2019).

Godbey et al., Size matters: Molecular weight affects the efficiency of poly(ethylenimine) as a gene delivery vehicle, J Biomed Mater Res., 45: 268-275 (1999).

Godbey et al., Tracking the intracellular path of poly(ethylenimine)/DNA complexes for gene delivery, Proc. Natl. Acad. Sci. U.S.A., 96: 5177-5181 (1999).

Gootenberg et al., Nucleic acid detection with CRISPR-Cas13a/C2c2, Science, 356(6336): 438-442 (2017).

Gory et al., The Vascular Endothelial-Cadherin Promoter Directs Endothelial-Specific Expression in Transgenic Mice, Blood, 93: 184-192 (1999).

Gothert JR, et al., Genetically tagging endothelial cells in vivo: bone marrow-derived cells do not contribute to tumor endothelium, Blood, 104:1769-1777 (2004).

Green and Sambrook, Molecular Cloning: A Laboratory Manual (Fourth Edition), Cold Spring Harbor Laboratory Press (Jun. 15, 2012).

Gregoriadis, G., Engineering liposomes for drug delivery: progress and problems, Trends Biotechnol., 13: 527-537 (1995).

Horvath and Barrangou, CRISPR/Cas, the immune system of bacteria and archaea, Science, 327: 167 (2010).

Howe, Insertional mutagenesis combined with acquired somatic mutations causes leukemogenesis following gene therapy of SCID-X1 patients, J. Clin. Invest. 118, 3143-3150 (2008).

Huang et al., Endothelial p110γPI3K Mediates Endothelial Regeneration and Vascular Repair After Inflammatory Vascular Injury, Circulation, 133: 1093-1103 (2016).

Jinek et al., A programmable dual-RNA-guided DNA endonuclease in adaptive bacterial immunity, Science, 337: 816 (2012).

Kim et al., CRISPR/Cpf1-mediated DNA-free plant genome editing, Nature Communications, 8 (14406): 14406 (2017).

Kitts et al., A method for producing recombinant baculovirus expression vectors at high frequency, Biotechniques, 14: 810-817 (1993).

(56) References Cited

OTHER PUBLICATIONS

Kung et al., Long Noncoding RNAs: Past, Present, and Future, Genetics, 193(3): 651-669 (2013).
Liong et al., Antimicrobial activity of silver nanocrystals encapsulated in mesoporous silica nanoparticles, Adv. Mater., 21: 1684-1689 (2009).
Lucklow et al., Efficient Generation of Infectious Recombinant Baculoviruses by Site-Specific Transposon-Mediated Insertion of Foreign Genes into a Baculovirus Genome Propagated in *Escherichia coli*, J. Virol, 67: 4566-4579 (1993).
Lucklow, Baculovirus systems for the expression of human gene products, Curr. Opin. Biotechnol, 4: 564-572 (1993).
Makadia HK, Siegel SJ., Poly Lactic-co-Glycolic Acid (PLGA) as Biodegradable Controlled Drug Delivery Carrier, Polymers, 3:1377-1397 (2011).
Makarova et al., Evolution and classification of the CRISPR-Cas systems, Nat. Rev. Microbiol., 9, 467 (2011).
Mali et al., RNA-Guided Human Genome Engineering via Cas9, Science 339, 823-826 (2013).
Manno et al., Successful transduction of liver in hemophilia by AAV-Factor IX and limitations imposed by the host immune response, Nat. Med., 12: 342-347 (2006).
Makarova, K.S. and E.V. Koonin, Annotation and classification of CRISPR-Cas systems, Methods Mol. Biol., 1311: 47-75 (2015).
Marchese et al., The multidimensional mechanisms of long noncoding RNA function, Genome Biol., 18: 206 (2017).
McBain et al., Polyethyleneimine functionalized iron oxide nanoparticles as agents for DNA delivery and transfection, J. Mater. Chem., 17: 2561-2565 (2007).
Mehta, D. and Malik, A.B., Signaling mechanisms regulating endothelial permeability, Physiol Rev, 86: 279-367 (2006).
Monahan-Earley et al., Evolutionary origins of the blood vascular system and endothelium, Thromb. Haemost., 11 Suppl 1: 46-66 (2013).
Munoz-Chapuli, The origin of the endothelial cells: an evo-devo approach for the invertebrate/vertebrate transition of the circulatory system, Evol. Dev., 7: 351-358 (2005).
Nelson et al., In vivo genome editing improves muscle function in a mouse model of Duchenne muscular dystrophy, Science 351, 403-407 (2016).
Park et al., Mannosylated polyethylenimine coupled mesoporous silica nanoparticles for receptor-mediated gene delivery, Int. J. Pharm., 359 :280-287 (2008).
Pensado et al., Current strategies for DNA therapy based on lipid nanocarriers, Expert Opin Drug Deliv., 11: 1721-1731 (2014).
Prandini et al., The human VE-cadherin promoter is subjected to organ-specific regulation and is activated in tumour angiogenesis, Oncogene, 24: 2992-3001 (2005).
Prosperi et al., Drug nanocarriers to treat autoimmunity and chronic inflammatory diseases, Semin. Immunol., 34, 61-67 (2017).
Rao J.P., Geckeler K.E., Polymer nanoparticles: Preparation techniques and size-control parameters, Progress in Polymer Science, 36: 887-913 (2011).
Raper et al., Fatal systemic inflammatory response syndrome in a ornithine transcarbamylase deficient patient following adenoviral gene transfer, Mol. Genet. Metab., 80: 148-158 (2003).
Sander et al., CRISPR-Cas systems for genome editing, regulation and targeting, Nat. Biotechnol., 32(4): 347-55 (2014).
Schlaeger et al., Vascular endothelial cell lineage-specific promoter in transgenic mice, Development, 121(4): 1089-98 (1995).
Torchilin, V.P., Recent advances with liposomes as pharmaceutical carriers, Nat Rev Drug Discov., 4: 145-160 (2005).
Torchilin, V.P., Micellar nanocarriers: pharmaceutical perspectives, Pharm Res., 24: 1-16 (2007).
Ulbrich et al., Targeted drug-delivery approaches by nanoparticulate carriers in the therapy of inflammatory diseases, J. R. Soc. Interface, 7 (Suppl. 1): S55-S66 (2010).
Urban-Klein et al., RNAi-mediated gene-targeting through systemic application of polyethylenimine (PEI)-complexed siRNA in vivo, Gene Ther., 12: 461-466 (2005).
Wang EC, Wang AZ, Integrative Biology: Quantitative Biosciences from Nano to Macro, 6(1): 9-26 (2014).
Wang et al., Biofunctionalized targeted nanoparticles for therapeutic applications, Expert Opinion on Biological Therapy, 8: 1063-1070 (2008).
Ware., L.B. and Matthay, M.A., The acute respiratory distress syndrome, N. Engl. J. Med., 342: 1334-1349 (2000).
Xia et al., Polyethyleneimine Coating Enhances the Cellular Uptake of Mesoporous Silica Nanoparticles and Allows Safe Delivery of siRNA and DNA Constructs, ACS Nano, 3(10): 3273-3286 (2009).
Yin et al., Structure-guided chemical modification of guide RNA enables potent non-viral in vivo genome editing, Nat Biotechnol 35, 1179-1187 (2017).
Zetsche et al., Cpf1 is a single RNA-guided endonuclease of a class 2 CRISPR-Cas system, Cell, 163: 759-771 (2015).
Zintchenko et al., Simple modifications of branched PEI lead to highly efficient siRNA carriers with low toxicity, Bioconjug Chem., 19: 1448-55 (2008).
International Search Report and Written Opinon, corresponding to PCT/US22/17501, dated Jun. 15, 2022.

* cited by examiner

A

| | Z-Ave | PdI | ZP |
|---|---|---|---|
| PLA10K-PEG | 62.89 | 0.277 | -14.8 |
| PLA10K-PEG-PEI1.5-0.5 | 70.4 | 0.358 | 28.2 |
| PLA10K-PEG-PEI3.0-0.5 | 61.02 | 0.203 | 22.1 |

B

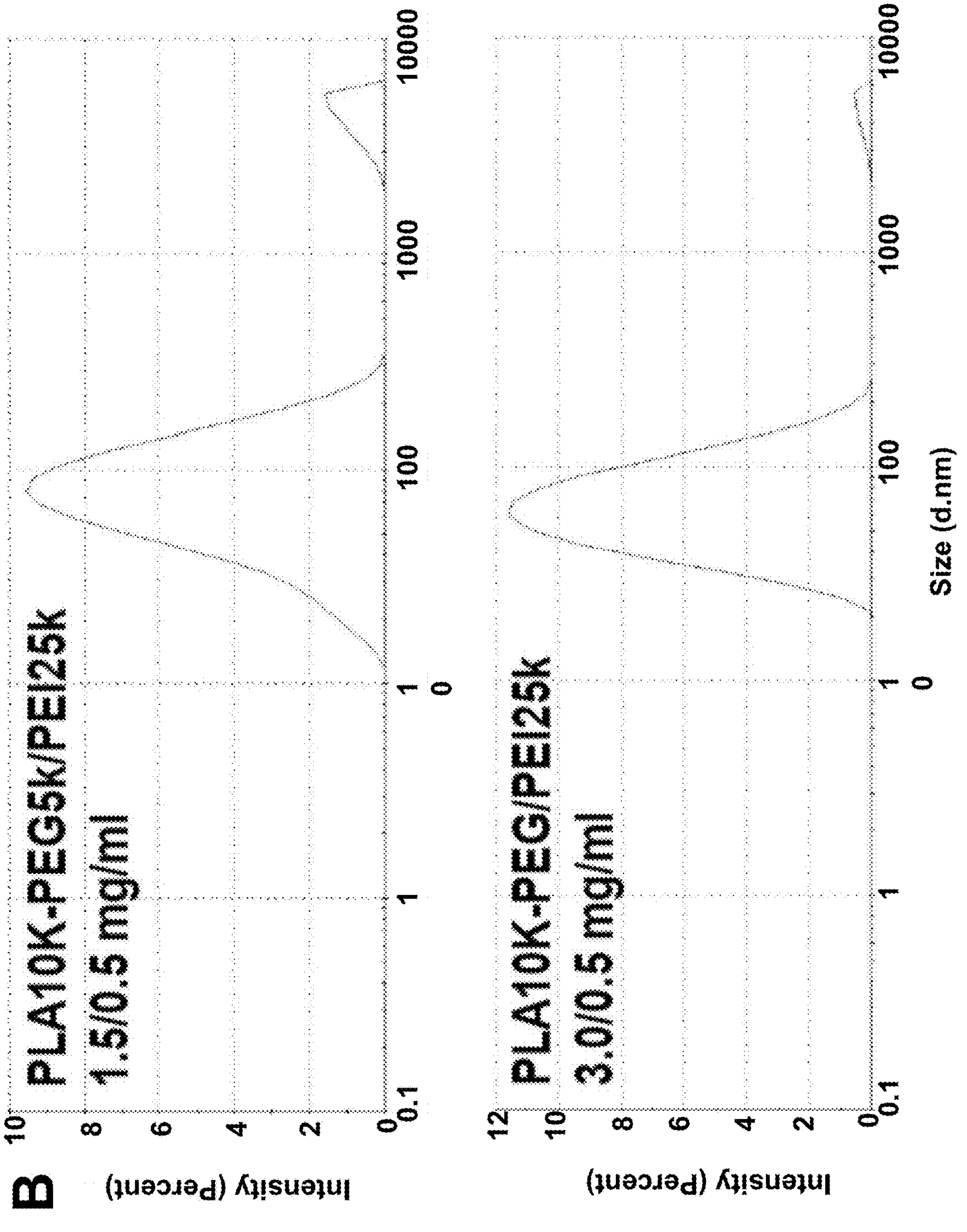
FIG. 2 (Continued; continuation of B)

A

| | Z-Ave | PdI | ZP |
|---|---|---|---|
| PLA35K-PEG | 100.8 | 0.076 | -17.4 |
| PLA35K-PEG+PEI25K 0.25-0.5 mg/ml | 117.4 | 0.193 | 32.6 |
| PLA35K-PEG+PEI25K 0.4-0.5 mg/ml | 118.4 | 0.165 | 29.3 |

B

PLA35k-PEG5k:PEI25k
0.4:0.5

PLA35k-PEG5k:PEI25k
0.3:0.5

CATIONIC POLYMER-FORMULATED NANOPARTICLES AND METHODS OF USE

CROSS-REFERENCE TO RELATED PATENT APPLICATIONS

The present application represents the National Stage entry of PCT/US2022/017501 filed on Feb. 23, 2022, which claims the benefit of priority to U.S. Provisional Application No. 63/152,815, filed on Feb. 23, 2021, the content of which is incorporated herein by reference in its entirety.

STATEMENT REGARDING FEDERALLY SPONSORED RESEARCH OR DEVELOPMENT

This invention was made with government support under HL123957, HL125350, HL133951, HL077806, and HL140409, awarded by the National Institutes of Health. The government has certain rights in the invention.

REFERENCE TO A SEQUENCE LISTING

This application is being filed electronically via EFS-Web and includes an electronically submitted Sequence Listing in .txt format. The .txt file contains a sequence listing entitled "702581_02102_ST25.txt" created on Apr. 4, 2022 and is 1,143 bytes in size. The Sequence Listing contained in this .txt file is part of the specification and is hereby incorporated by reference herein in its entirety.

FIELD

The disclosure is directed nanoparticles comprising polyethylene glycol (PEG)-b-poly (D,L-lactide) (PLA) (PEG-b-PLA, PLA-PEG)) copolymer or a PEG-b-poly(lactic acid-co-glycolic acid) (PLGA) (PEG-b-PLGA, PLGA-PEG) copolymer which is formulated with a cationic polymer, such as polyethylenimine (PEI) for the delivery of nucleic acid molecules. The disclosed nanoparticles are distinguished from surface PEGylated nanoparticles, where the raw material of the disclosed nanoparticles comprises a PEG-containing copolymer and the disclosed nanoparticles do not require PEG surface-coating.

BACKGROUND

The efficient delivery of nucleic acids, such as DNA and RNA to cultured cells or to live animals and humans is critically important for biomedical research and the development of therapeutic agents for various diseases. DNA and RNA that are delivered to live animals and humans or cultured cells may include plasmid DNA and its derivatives such as minicircle DNA, nanoplasmid, and small interfering RNA (siRNA), antisense RNA, microRNA (miRNA), and long-noncoding RNA (lncRNA).

Despite the efficacy of viral vectors for gene delivery, viral vectors may induce immune responses and other severe side effects which limit their clinical utility. (See Raper et al., Mol. Genet. Metab., 80: 148-158 (2003); Manno et al., Nat. Med., 12: 342-347 (2006); and Howe, J. Clin. Invest. 118, 3143-3150 (2008)). For example, adeno-associated virus (AAV)-mediated delivery of the CRISPR/Cas9 system permits rapid genome editing in animals but is problematic for several reasons. (See Cox et al., Nat Med 21, 121-131 (2015); Yin et al., Nat Biotechnol 35, 1179-1187 (2017); Nelson et al., Science 351, 403-407 (2016); and *Mali* et al., Science 339, 823-826 (2013). First, the AAV vector is highly immunogenic and has a low packaging capacity which is restricted to ~4.7 kb in AAVs. (See Nelson et al., supra; and Carroll et al., Proc Natl Acad Sci USA 113, 338-343 (2016)). Second, extended expression of Cas9 from AAV may cause unwanted DNA damage.

To circumvent the disadvantages associated with viral vector delivery systems, non-viral gene delivery methods and reagents have been explored, including liposomes, polycationic polymers, and organic or inorganic nanoparticles. While some of these systems exhibit improved safety profiles, many are limited by low gene transfer efficiency both in vitro and in vivo and are observed to accumulate in the liver. In addition, many of these systems are not capable of cell-specific gene delivery, which is especially needed for treating various types of diseases including cardiovascular diseases and cancer. Thus, there remains an unmet need for compositions and methods that efficiently deliver genes to specific cell types such as vascular endothelial cells in vivo with limited associated toxicity to treat various diseases associated with vascular endothelial dysfunction.

SUMMARY

Provided herein is a composition comprising: (a) a nanoparticle comprising a poly(D,L-Lactide) (PLA)-b-polyethylene glycol (PEG) (PLA-b-PEG, PLA-PEG) copolymer or a poly(lactic acid-co-glycolic acid) (PLGA)-b-polyethylene glycol (PEG) (PLGA-b-PEG, PLGA-PEG) copolymer and specifically formulated with polyethylenimine (PEI) including modified large molecular weight PEI, or crosslinked small molecular weight PEI (for example as a coating on the nanoparticle, at a unique ratio), and (b) one or more cargo molecules associated with the nanoparticle. Also provided herein is a method of delivering one or more cargo molecules to a cell, especially the vascular endothelial cells in vivo, which comprises contacting the cell with the aforementioned composition.

DETAILED DESCRIPTION

Figure 1:
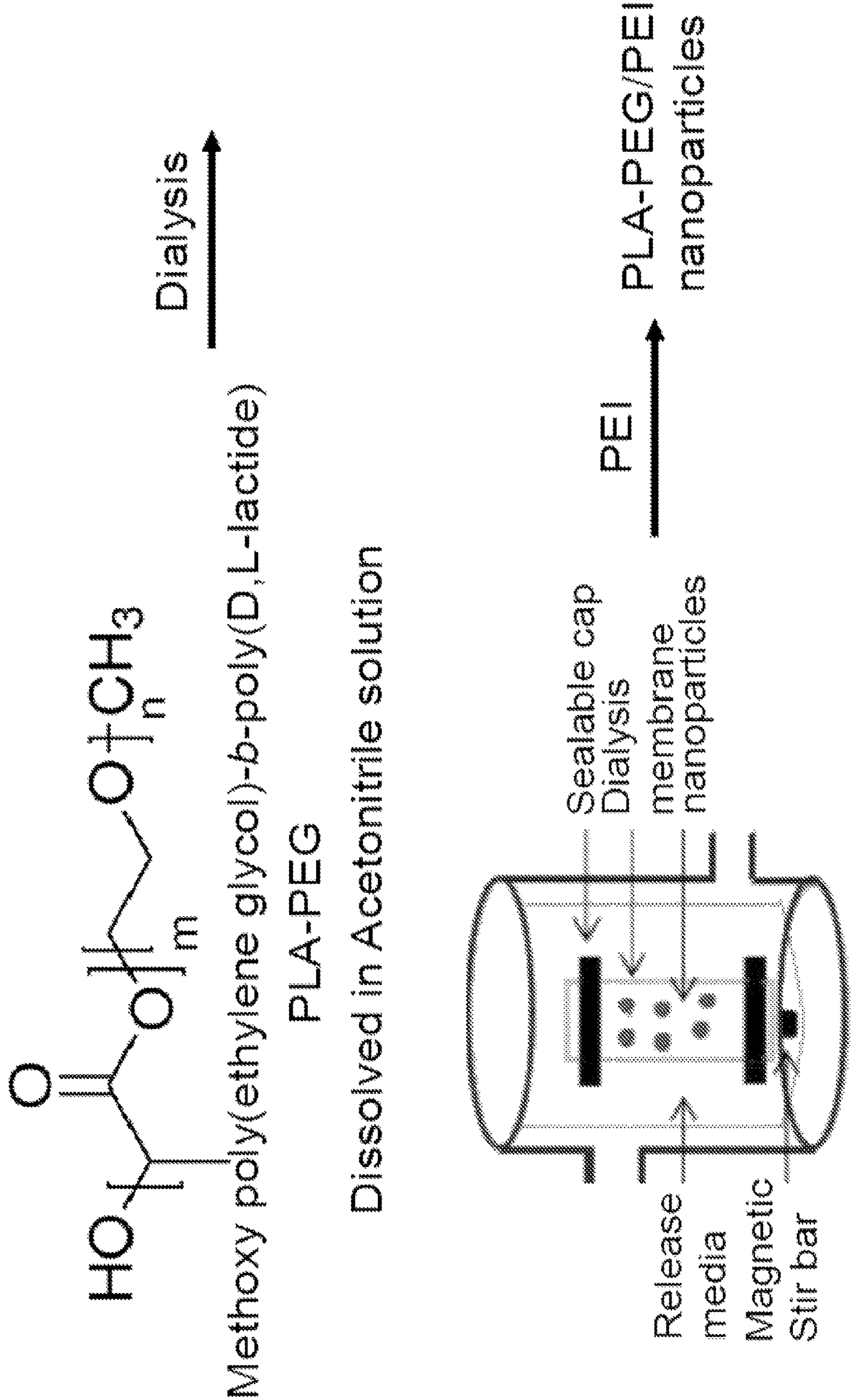
FIG. 1 is a schematic diagram which illustrates the preparation of PEI-coated PLA-PEG (PLA-PEG/PEI) nanoparticles using a dialysis method.

The present disclosure is predicated, at least in part, on the discovery that polyethylenimine (PEI)-coated nanoparticles comprising polyethylene glycol (PEG)-b-poly(D,L-lactide) (PLA) (PLA-b-PEG) copolymer (e.g., block co-polymer) with specific formulation different from PEI-coated PLGA-PEG nanoparticles are capable of delivering nucleic acids into cultured cells with an efficiency similar to or greater than more widely used transfection reagents (e.g., lipofectamine) and uniquely into live animals and human subjects with high efficiency in vascular endothelial cells. These nanoparticles are distributed throughout the entire organism, instead of concentrating in the liver as observed for other lipid nanoparticles and recombinant viral vectors. It will also be appreciated that the disclosed nanoparticles can be engineered to harness optimal targeting of drugs to vascular endothelial cells and various tissues and to optimize drug-loading capacity, allowing for improved pharmacokinetics, safe and effective drug delivery, and enhanced bioavailability of therapeutics (Ulbrich et al., *J. R. Soc. Interface,* 7 (Suppl. 1): S55-S66 (2010); and Prosperi et al., *Semin. Immunol.,* 34, 61-67 (2017)).

The term "nanoparticle," as used herein, refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, 1000 nm, and all integers and fractional integers in between). In some embodiments, the nanoparticle has at least one dimension, e.g., a diameter, of about 100 nm. In other embodiments, the nanoparticle has a diameter of about 200 nm, a diameter of about 500 nm, or a diameter of about 1000 nm (1 m). The disclosed nanoparticles may have an effective diameter of about 50 nm to about 500 nm, including any integer value between 50 nm and 500 nm (including about 50, 60, 70, 80, 90, 100, 200, 500, and all integers and fractional integers in between) Nanoparticles having a diameter of at least 1000 nm also may be referred to as a "microparticles." Thus, the term "microparticles" includes particles having at least one dimension in the range of about one micrometer (m), i.e., $1\times10^{-6}$ meters, to about 1000 m. The term "particle" as used herein is meant to include nanoparticles and microparticles.

Nanoparticles suitable for use in the presently disclosed compositions and methods may exist in a variety of shapes, including, but not limited to, spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes. In some embodiments, the disclosed nanoparticles have a spherical shape.

The nanoparticle may be of any composition that is suitable for efficient delivery of nucleic acids to cells. Several different types of nanoparticles have been developed that are suitable for nucleic acid delivery, including, for example, lipid-based nanoparticles (Pensado et al., *Expert Opin Drug Deliv.,* 11: 1721-1731 (2014)), polymer-based nanoparticles (Gao et al., *Acta Biomater,* 25: 184-193 (2015)), and inorganic nanoparticles.

Lipid-based nanoparticles are composed of physiological lipids. Hence, lipid-based nanoparticles are well tolerated, usually nontoxic, and are degraded to a nontoxic residue. Liposomes were one of the first developed lipid-based carriers characterized to be non-toxic, flexible, biocompatible, and completely biodegradable. (See, e.g., Akbarzadeh et al., *Nanoscale Res. Lett.,* 8: 102 (2013)). Liposomes are primarily composed of phospholipid bilayer vesicles containing phosphatidylcholine and phosphatidylethanolamine, the most common phospholipids found in nature, with other membrane bilayer constituents, such as cholesterol and hydrophilic polymers around each liposomal vesicle. (See Gregoriadis, G., *Trends Biotechnol.,* 13: 527-537 (1995); and Chuang et al., *Nanomaterials,* 8: 42 (2018)). To enhance their circulation half-life and stability in vivo, liposomes may be conjugated with biocompatible polymers such as polyethylene glycol (PEG). (See Torchilin, V. P., *Nat Rev Drug Discov.,* 4: 145-160 (2005)). Liposomes can also be functionalized with targeting ligands to increase the accumulation of diagnostic and therapeutic agents within target cells.

Polymer-based nanoparticles typically are formed from biocompatible and biodegradable block co-polymers of different hydrophobicity. (See Chan et al., In: *Cancer Nanotechnology*; Grobmyer S R, Moudgil B M, editors. Vol. 624. Humana Press; 2010. pp. 163-175)). These copolymers spontaneously assemble into a core-shell micelle formation in an aqueous environment. (See Torchilin, V. P., Pharm Res., 24: 1-16 (2007)). Polymeric nanoparticles have been formulated to encapsulate hydrophilic and/or hydrophobic small drug molecules, as well proteins and nucleic acid macromolecules. (See Wang et al., Expert Opinion on Biological Therapy, 8: 1063-1070 (2008)). Several polymer-based nanoparticles, such as, for example, poly(lactic-co-glycolic acid) or poly(lactide-co-glycolide) (PLGA), polylactic acid or polylactide (PLA), poly glycolic acid or polyglycolide (PGA), polycaprolactone (PCL), poly (D,L-lactide) (PDLLA), chitosan, and Peglyated PLGA or PLA have been developed for drug delivery and are in various stages of clinical trials. (See Devulapally R, Paulmurugan R., "Polymer nanoparticles for drug and small silencing RNA delivery to treat cancers of different phenotypes," Wiley Interdisciplinary Reviews. Nanomedicine and Nanobiotechnology. 2014; 6(1): 10.1002/wnan.1242. doi: 10.1002/wnan.1242) but they are not efficient in targeting vascular endothelial cells.

Inorganic nanoparticles exhibit different capabilities depending on the chemical composition of their cores. A wide variety of inorganic nanoparticles are used in the art for biological applications. For example, semiconductor quantum dots are commercially available and offer an alternative to fluorescently labeled particles, while iron oxide nanoparticles have been approved for human use in magnetic resonance imaging (MRI) applications as contrast enhancers. Gold nanoparticles offer many size-dependent and shape-dependent optical and chemical properties, biocompatibility, and facile surface modification. (See Wang E C, Wang A Z, Integrative Biology: Quantitative Biosciences from Nano to Macro, 6(1): 9-26 (2014)).

Nanoparticles Comprising (PEG)-b-poly(D,L-lactide) (PLA) (PEG-b-PLA) Co-Polymer

In some embodiments, the disclosed nanoparticles comprise polyethylene glycol (PEG)-b-poly (D,L-lactide) (PLA) (PEG-b-PLA) co-polymer (referred to herein as "PLA-PEG" nanoparticles). PLA is a widely-used polymer in nanoparticles due to its biocompatibility, low toxicity, and well-documented utility for sustained drug release. PLA has been approved by U.S. Food and Drug Administration and the European Medicine Agency for human use, and PLA or PLA-based nanoparticles have been widely employed for small molecule drug delivery applications. (See, e.g., Dinarvand et al., *International Journal of Nanomedicine,* 6: 877-895 (2011); and Makadia H K, Siegel S J., *Polymers,* 3:1377-1397 (2011)). PLA breaks down into body metabolites, e.g. lactic acid, by hydrolysis of ester bonds, which are removed in the Kreb cycle. The PLA-PEG co-polymer is a biocompatible, amphiphilic block copolymer composed of a hydrophilic PEG block and a hydrophobic PLA block. These materials have been used in controlled release and nanoparticle formulation for drug encapsulation and delivery applications.

PLA-PEG nanoparticles may be prepared using any suitable method known in the art for preparing polymer-based nanoparticles. Such methods include, but are not limited to, dialysis, nanoprecipitation, salting out, and supercritical fluid techniques. (See Rao J. P., Geckeler K. E., *Progress in Polymer Science,* 36: 887-913 (2011). In addition, PLA-b-PEG raw material and PLA-PEG nanoparticles are commercially available from a variety of sources and may be used in the context of this disclosure.

PLA and PEG of any suitable molecular weight may be employed in the nanoparticle, and both are commercially available over a wide range of molecular weights (e.g., between about 1,000 to about 100,000 g/mol). For example, the PLA molecular weight may be 5,000, 10,000, 15,000, 20,000, 25,000, 30,000, 35,000, 40,000, 45,000, 50,000, 55,000, 60,000, 65,000, 70,000, 80,000, 90,000, 100,000 g/mol, or a range defined by any of the two foregoing values. The PEG molecular weight may be, for example, between about 2000 g/mol to about 20,000 g/mol (e.g., about 2,000, 3,000, 4,000, 5,000, 6,000, 7,000, 8,000, 9,000, 10,000 g/mol, or a range defined by any two of the foregoing values).

In some embodiments, the PLA-PEG nanoparticle is coated or formulated with a cationic polymer, such as polyethylenimine (PEI). PEI is a synthetic cationic polymer with a repeating unit composed of an amine group and two carbon aliphatic CH2CH2 spacer. Large molecular weight PEI, e.g., PEI25k binds and compact DNA and RNA into complexes that are effectively taken up in cells, and therefore PEI has been used in nucleic acid delivery but large MW PEI is not quite efficient in delivering nuclei acids and has high cell toxicity. (See Boussif et al., *Proc. Natl. Acad. Sci. U.S.A.;* 92: 7297-7301 (1995); Godbey et al., *Proc. Natl. Acad. Sci. U.S.A.,* 96: 5177-5181 (1999); Urban-Klein et al.,

*Gene Ther.,* 12: 461-466 (2005); Xia et al., *ACS Nano,* 3(10): 3273-3286 (2009)). PEI also can be attached to nanoparticle surfaces through covalent and electrostatic interactions. (See Park et al., *Int. J. Pharm.,* 359:280-287 (2008); Elbakry et al., *Nano Lett.,* 9: 2059-2064 (2009); Fuller et al., *Biomaterials,* 29: 1526-1532 (2008); McBain et al., *J. Mater. Chem.,* 17: 2561-2565 (2007); and Liong et al., *Adv. Mater.,* 21: 1684-1689 (2009)). The present inventors have determined that coating PLA-PEG nanoparticles with a polymer such as PEI greatly facilitate delivery of nucleic acids such as DNA and RNA and allow for nanoparticle targeting to cells, especially vascular endothelial cells in vivo with minimal cell toxicity (such as, e.g., for in vivo genome editing applications, or gene expression modifications). PEI of any suitable molecular weight may be employed to coat the disclosed nanoparticles, and PEI is commercially available over a wide range of molecular weights (e.g., 400, 600, 800, 1,200, 1,800, 5,000, 10,000, 25,000, 30,000, 35,000, 40,000, 45,000, 50,000 Da).

In some embodiments, the PEI may be modified (e.g., via succinylation or acetylation) to lower its potential toxicity or increase its nucleic acid condensation capacity. It will be appreciated that succinylation can lower the potential toxicity of large molecular weight PEI. (See Zintchenko et al., *Bioconjug Chem.,* 19: 1448-55 (2008). Although large molecular weight PEIs (e.g., 25 k Da or greater) are potentially toxic due to their aggregation and difficulty degrading, low molecular weight PEIs (e.g. MW~400, 600, 800, 1200, 1800-2000 Da) are well tolerated, but have low binding capacity for nucleic acids. (See Godbey et al., *J Biomed Mater Res.,* 45: 268-275 (1999); Breunig et al., *Proc Natl Acad Sci USA,* 104: 14454-14459 (2007)).

In some embodiments, the composition described herein comprises low molecular weight PEI e.g., PEI400, 600, 800, 1200, and 1800 Da formulated directly with the PLA-PEG or PLGA-PEG nanoparticle (e.g., 75:1 PEI600:PLGA-PEG), which increases nucleic acid binding capacity to levels similar to large molecular weight PEI.

In other embodiments, the PEI polymer is a cross-linked, low molecular weight PEI (cPEI), e.g. crosslinked PEI400, 600, 800, 1200, and 1800 Da, which are cross-linked via various crosslinkers (e.g., diacrylate, disulfide, and disimine, as well as carbamate, amide, ketal linkages).

In some embodiments, the cationic polymer for formulating with PLA-PEG or PLGA-PEG nanoparticles is chitosan, poly(2-(dimethylamino)ethyl methacrylate), poly (aminoester)s such as polymers formed by reacted an acrylate and an amine via Michael addition, dendrimers, polylysines and other poly(amino acids) such as amino acids that are positively charged at physiological pH (e.g., a pH of about 6-8, such as a pH of about 7).

The composition described herein comprises one or more cargo molecules associated with the nanoparticle. The terms "cargo" or "cargo molecule," as used herein, refer to any entity (e.g. a small molecule, macromolecule or macromolecular complex), which may be delivered/transferred/is transferable across the membrane of a cell or into the cytosol or nucleus of a target cell via the nanoparticle. When two entities are "associated with" one another, as described herein, they are linked by a direct or indirect covalent or non-covalent interaction. In certain embodiments, the association is covalent. Ideally, the association is non-covalent. Suitable non-covalent interactions include, but are not limited to, hydrogen bonding, van der Waals interactions, hydrophobic interactions, magnetic interactions, electrostatic interactions, etc. In some embodiments, the association is electrostatic. In some embodiments, the one or more cargo molecules is one or more nucleic acid molecules. The terms "nucleic acid molecule," "nucleic acid sequence," and "polynucleotide" are synonymous and are intended to encompass a polymer of DNA or RNA, which can be single-stranded or double-stranded and which can contain non-natural or altered nucleotides. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

The one or more nucleic acid molecules may be DNA, RNA, or combinations thereof (e.g., a DNA/RNA hybrid). In some embodiments, the nucleic acid molecule is a plasmid. The term "plasmid," as used herein, refers to a small DNA molecule within a cell that is physically separated from a chromosomal DNA and can replicate independently (i.e., as an "episome"). Plasmids occur naturally in bacteria, archaea, and other eukaryotic organisms and commonly exist as small circular double-stranded DNA molecules. Synthetic plasmids are widely used in the art as vectors in molecular cloning, driving the replication of recombinant DNA sequences within host organisms. Plasmid DNA may be generated using routine molecular biology techniques, such as those described in, e.g., Green and Sambrook, *Molecular Cloning: A Laboratory Manual* (*Fourth Edition*), Cold Spring Harbor Laboratory Press (Jun. 15, 2012) or may be obtained from commercial sources.

In other embodiments, the one or more nucleic acid molecules may be a minicircle DNA. The term "minicircle DNA," as used herein, refers to small excised, circular DNA fragments from a parental plasmid which is in generally free of bacterial plasmid DNA sequences. Minicircle DNA is used in the art as a vector for gene transfer into mammalian cells and has the advantage of reduced immunogenicity due to the lack of bacterial DNA sequences. (See Gaspar et al., *Expert Opin Biol Ther.,* 15(3):353-79 (2015)).

In other embodiments, the one or more nucleic acid molecules may be a nanoplasmid DNA. The term "nanoplasmid DNA," as used herein, refers to plasmid DNA with the elimination of the antiquated bacterial backbones. Nanoplasmid is used in the art as a vector for gene transfer and gene therapy.

The plasmid or minicircle or nanoplasmid DNA may be any suitable recombinant plasmid that comprises a heterologous nucleic acid sequence to be delivered to a target cell, either in vitro or in vivo. The heterologous nucleic acid sequence may encode a gene product (e.g., a protein) of interest for the purposes of, for example, disease treatment or prevention, and may optionally be in the form of an expression cassette. The term "recombinant" refers to a polynucleotide of semisynthetic, or synthetic origin which either does not occur in nature or is linked to another polynucleotide in an arrangement not found in nature. The term "heterologous," as used herein refers to a nucleic acid sequence obtained or derived from a genetically distinct entity from the rest of the entity to which it is being compared.

In some embodiments, the nucleic acid molecule associated with the nanoparticle is a DNA plasmid or minicircle or nanoplasmid DNA that comprises one or more nucleic acid sequences that express a gene (or genes) of interest to mediate genome editing or modification of a target gene or modulation of the expression levels of target gene(s). For example, the DNA plasmid or minicircle or nanoplasmid DNA may encode and express components of the genome editing system, e.g., the CRISPR/Cas9 gene editing system, base editors, prime editing system, TALEN system. CRISPR/Cas gene editing systems have been developed to enable targeted modifications to a specific gene of interest in eukaryotic cells. CRISPR/Cas gene editing systems are based on the RNA-guided Cas9 nuclease from the type II prokaryotic clustered regularly interspaced short palindromic repeats (CRISPR) adaptive immune system. (See, e.g., Jinek et al., *Science,* 337: 816 (2012); Gasiunas et al., *Proc. Natl. Acad. Sci. U.S.A.,* 109, E2579 (2012); Garneau et al., *Nature,* 468: 67 (2010); Deveau et al., *Annu. Rev. Microbiol.,* 64: 475 (2010); Horvath and Barrangou, *Science,* 327: 167 (2010); Makarova et al., *Nat. Rev. Microbiol.,* 9, 467 (2011); Bhaya et al., *Annu. Rev. Genet.,* 45, 273 (2011); Cong et al., *Science,* 339: 819-823 (2013); and U.S. Pat. Nos. 8,697,359; 8,795,965; and 9,322,037). The CRISPR/Cas9 system is extensively used in the art to edit the genome of zygotes to generate various genetically modified animal species, including mice, and rats. The use of CRISPR/Cas9 in postnatal or adult animals including canines and monkeys also is under investigation. (See Cong et al., *Science* 339, 819-823 (2013); Cox et al., supra, Doudna et al., *Science,* 346: 1258096 (2014); and Yin et al., supra). In addition to CRISPR/Cas9 systems, the nanoparticle composition described herein may be used to deliver other CRISPR/Cas systems known in the art, including, for example, CRISPR/Cas13, which induces RNA knockdown. (Zetsche et al., Cell, 163: 759-771 (2015)) and CRISPR/Cpf129 (Kim et al., Nature Communications, 8 (14406): 14406 (2017)), and base editors (Gehrke et al., *Nature Biotechnology,* 37: 224-226 (2019)), and prime editing (Anzalone et al., *Nature,* 576: 149-157 (2019)). CRISPR/Cas systems suitable for use in connection with the present disclosure are further described in, e.g., Marakova, K. S. and E. V. Koonin, *Methods Mol. Biol.,* 1311: 47-75 (2015); Sander et al., *Nat. Biotechnol.,* 32(4): 347-55 (2014); and Gootenberg et al., *Science,* 356 (6336): 438-442 (2017)).

In other embodiments, the one or more nucleic acid molecules may be an RNA molecule. For example, the RNA molecule may be a messenger RNA (mRNA) sequence that encodes a protein. Alternatively, the RNA molecule may be non-protein coding. For example, the RNA molecule may comprise a nucleic acid sequence that is capable of inducing RNA interference (RNAi). The term "RNA interference" refers to a process in which RNA molecules inhibit gene expression or translation by neutralizing targeted mRNA molecules. To achieve an RNAi effect, for example, RNA having a double strand structure containing the same base sequence as that of the target mRNA may be used. Two types of small RNA molecules may induce RNAi: microRNA (miRNA) and small interfering RNA (siRNA). miRNA is a small non-coding RNA molecule (containing about 22 nucleotides) found in plants, animals and some viruses, which silences complementary target sequences by one or more of the following processes: (1) cleavage of the target mRNA strand into two pieces, (2) destabilization of the mRNA through shortening of its poly(A) tail, and (3) less efficient translation of the mRNA into proteins by ribosomes. (See Bartel D. P., *Cell,* 136 (2): 215-233 (2009); and Fabian et al., *Annual Review of Biochemistry,* 79: 351-79 (2010)). siRNA (also known as short interfering RNA or silencing RNA), is a class of double-stranded RNA molecules, typically 20-25 base pairs in length, which silence complementary target sequences by degrading mRNA after transcription, preventing translation. (See Dana et al., *International Journal of Biomedical Science,* 13(2):48-57 (2017); and Agrawal, et al., *Microbiol. Mol. Biol. Rev.,* 67: 657-685 (2003)). siRNA can also act in RNAi-related pathways in an antiviral mechanism or play a role in the shaping of the chromatin structure of a genome. Any RNA molecule that is capable of silencing gene expression of a target gene may be used in connection with the present disclosure. In some embodiments, the RNA molecule is siRNA, miRNA, antisense oligoes. In other embodiments, the RNA molecule may a long non-coding RNA (lncRNA). Long non-coding RNAs are a large and diverse class of transcribed RNA molecules with a length of more than 200 nucleotides that do not encode proteins. lncRNAs are thought to encompass nearly 30,000 different transcripts in humans, and account for the major part of the non-coding transcriptome. While the mechanism of action of lncRNAs is under investigation, lncRNAs appear to be important regulators of gene expression, and lncRNAs are thought to have a wide range of functions in cellular and developmental processes. lncRNAs may carry out both gene inhibition and gene activation through a range of diverse mechanisms (see, e.g., Kung et al., Genetics, 193(3): 651-666 (2013); and Marchese et al., Genome Biol., 18: 206 (2017)).

The nucleic acid molecule may comprise a nucleic acid sequence that is operatively linked to a promoter; however, nucleic acid sequences that lack a promoter are also within the scope of the present disclosure. As used herein, a "promoter" is a DNA sequence that directs the binding of RNA polymerase, thereby promoting RNA synthesis. A nucleic acid sequence is "operably linked" or "operatively linked" to a promoter when the promoter is capable of directing transcription of that nucleic acid sequence. A promoter can be native or non-native to the nucleic acid sequence to which it is operably or operatively linked. Techniques for operably linking sequences together are well known in the art. The promoter may be a ubiquitous promoter. The term "ubiquitous promoter," as used herein, refers to a regulated or unregulated promoter that allows for continual transcription of its associated gene in a variety of cell types. Suitable ubiquitous promoters are known in the art and can be used in connection with the present disclosure. In other embodiments, the promoter may be a tissue-specific or cell-specific promoter. The terms "tissue-specific promoter" and "cell-specific promoter," as used herein, refer to a promoter that is preferentially activated in a given tissue or cell and results in expression of a gene product in the tissue or cell where activated. A tissue-specific or cell-specific promoter can be chosen based upon the target tissue or cell-type in which the nucleic acid sequence is to be expressed. In some embodiments, the nucleic acid molecule comprises a nucleic acid sequence that is operatively linked to an endothelial cell-specific promoter. Endothelial cell-specific promoters are known in the art. (See, e.g., Schlaeger et al., *Development,* 121(4): 1089-98 (1995); Dai et al., *J. Virol.,* 78(12): 6209-6221 (2004)), and include, for example the CDH5 promoter, which is the promoter of the human vascular endothelial-cadherin (CDH5) gene (see Gory et al., *Blood,* 93: 184-192 (1999); Huang et al., *Circulation,* 133: 1093-1103 (2016); and Prandini et al., *Oncogene,* 24: 2992-3001 (2005)), a Tie2 promoter (Fadel et al., *Biochem J.,* 330 (Pt 1): 335-43 (1998)), or the 5' endothelial enhancer of the stem cell leukemia locus (Gothert J R, et al., Blood, 104: 1769-1077 (2004)), or other organ restricted endothelial cell-specific promoter, e.g., lung EC-specific, or heart EC-specific promoter The nucleic acid molecule, PLA-PEG nanoparticle, and PEI may be combined in any desired ratio (in terms of weight or molarity). Exemplary ratios of PLA35k-PEG5k nanoparticle:PEI include, but are not limited to, 1:1, 1:5, 2:5, 3:5, 4:5, 6:5, 8:5, and the like for large molecular weight (MW) PEI, e.g., PEI25k, or modified PEI25k, e.g., succinylated PI25k or 1:5, 1:10, 1:20, 1:30, 1:40, 1:50, 1:60, 1:70, 1:80, 1:90, 1:100 and the like for low MW PEI (e.g. MW600, 800, 1200, 1800-2000 Da), or 1:1, 4:5, 4:7, 4:10, 4:12, 4:15 and the like for crosslinked low MW PEI (cPEI) with MW cut off 7 k Da for dialysis; or 1:1, 4:5, 4:7, 4:10, 4:15, 4:20 and the like for crosslinked low MW cPEI with MW cutoff 3.5 k Da for dialysis. Exemplary ratios of nucleic acid molecule (μg):PLA-PEG/PEI (μl) nanoparticles include, but are not limited to. 1:1, 1:2, 1:3, 1:4, 1:5 and the like. In some embodiments, the ratio of nucleic acid molecule:PLA-PEG nanoparticle:PEI may be about 1 μg:0.5-5 μg:0.5-5 μg, such as, for example, about 1 μg DNA:1.2 μg PLA35k-PEG5k:1.5 μg of PEI25 k Da, 1 μg DNA:1.2 μg PLA35k-PEG5k:45 μg of PEI600 Da or 1 μg:1.2 μg:2.1 μg of cPEI cutoff 7 k Da, or 1 μg:1.2 μg:3 μg of cPEI cutoff 3.5 k.

The nucleic acid molecule, PLGA-PEG nanoparticle, and PEI may be combined in any desired ratio (in terms of weight or molarity). Exemplary ratios of PLGA55k-PEG5k nanoparticle:PEI include, but are not limited to, 20:50, 20:75, 20:100, 22:50, 22:75, 22:100, 25:50, 25:75, 25:100 25:100, and the like for large MW PEI, e.g., PEI25k, modified PEI25k, e.g., succinylated PEI25k; or 2-2.55:20, 2-2.5:50, 2-2.5:100, 2-2.5:150, 2-2.5:200, 2-2.5-250, 2-2.5-300, 2-2.5-350, 2-2.5:400, and the like for low MW PEI (e.g., MW600, 800, 1200, 1800); and 2:5, 2:7, 2:10, 2:12, 2:15, 2:20, 2:25 and the like for crosslinked low MW cPEI with MW cut off 7 k or 3.5 k for dialysis. Exemplary ratios of nucleic acid molecule (μg):PLGA55k-PEG5k/PEI25k (μl) nanoparticles include, but are not limited to. 1:2, 1:3, 1:4, 1:5 and the like. In some embodiments, the ratio of nucleic acid molecule:PLGA-PEG nanoparticle:PEI may be about 1 μg:0.4-2 μg:0.5-5 μg, such as, for example, about 1 μg:0.66 μg:1.5 μg of PEI25 k Da, 1 μg:0.66 μg:45 μg of PEI600 Da or 1 μg:0.66 μg:2.1 μg of cPEI cutoff 7 k Da, or 1 μg:0.66 μg:3 μg of cPEI cutoff 3.5 k.

In some embodiments, the cargo molecule may be one or more small molecule compounds, with or without an associated nucleic acid molecule (as described herein). The term "small molecule compound," as used herein, refers to organic compounds, whether naturally-occurring or artificially created (e.g., via chemical synthesis) that have relatively low molecular weight and that are not proteins, or nucleic acids. Typically, small molecules have a molecular weight of less than about 1500 g/mol. Also, small molecules typically have multiple carbon-carbon bonds. A large number of naturally-occurring and synthetic small molecule compounds are known in the art and used as therapeutic agents against a wide variety of diseases. Examples of naturally-occurring small molecule compounds include, but are not limited to, penicillin, erythromycin, taxol, cyclosporin, and rapamycin. Examples of synthetic small molecule compounds include, but are not limited to, ampicillin, methicillin, sulfamethoxazole, and sulfonamides. Any suitable small molecule compound may be associated with the nanoparticle. In some embodiments, the PEI-coated PLA-PEG nanoparticle can be used to co-deliver one or more nucleic acid molecules and one or more small molecule compounds. For example, a small molecule compound may be encapsulated within a PLA-PEG nanoparticle, which may then be coated with PEI and associated with a nucleic acid molecule of interest.

The disclosure also provides a method of delivering one or more cargo molecules to a cell, which comprises contacting the cell with the nanoparticle composition described herein. Descriptions of PLA-PEG nanoparticles, PEI, cargo molecules, nucleic acid molecules, small molecule compounds, and components thereof described herein also are applicable to those same aspects of the aforementioned method of delivering one or more nucleic acid molecules to a cell.

The cell may be contacted with the nanoparticle composition in vitro or in vivo. The term "in vivo" refers to a method that is conducted within healthy or diseased living organisms in their intact state, while an "in vitro" method is conducted using components of an organism that have been isolated from its usual biological context. When the cell is contacted with the nanoparticle in vitro, the cell desirably is a eukaryotic cell. Suitable eukaryotic cells are known in the art and include, for example, insect cells, and mammalian cells including immortal cell lines and cancer cells. Suitable insect cells are described in, for example, Kitts et al., Biotechniques, 14: 810-817 (1993); Lucklow, Curr. Opin. Biotechnol, 4: 564-572 (1993); and Lucklow et al., J. Virol, 67: 4566-4579 (1993), and include Sf-9 and HI5 (Invitrogen, Carlsbad, CA).

When the cell is contacted with the nanoparticle composition in vivo, the composition desirably is a pharmaceutically acceptable (e.g., physiologically acceptable) composition, which comprises the nanoparticle and the associated one or more nucleic acid molecules, with or without a carrier, preferably a pharmaceutically acceptable (e.g., physiologically acceptable) carrier. Any suitable carrier can be used within the context of the disclosure, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., Remington: The Science and Practice of Pharmacy, 21st Edition, Lippincott Williams & Wilkins, Philadelphia, PA (2001).

The composition may be administered to an animal, such as a mammal, particularly a human, using standard administration techniques, including intravenous, subcutaneous, pulmonary, transdermal, intramuscular, intranasal, buccal, sublingual, suppository, or inhalational administration. The composition preferably is suitable for parenteral administration. The term "parenteral," as used herein, includes intravenous, intramuscular, intracardial, subcutaneous, inhalational, rectal, and vaginal administration. In other embodiments, the composition may be administered to a mammal using peripheral systemic delivery by intravenous or subcutaneous injection.

Applications

The disclosed subject matter has applications which include, but are not limited to: (i) in vitro cell culture transfection with nucleic acids including plasmid DNA and its derivatives, minicircle DNA, nanoplasmid, and RNAs such as siRNA, miRNA, lncRNA, antisense; (ii) in vivo delivery of nucleic acids including plasmid DNA, minicircle DNA, nanoplasmid, and RNAs such as siRNA, miRNA, lncRNA, antisense to cells in live animals and humans and modification of gene expression and function in vivo; (iii) in vivo delivery of plasmid DNA containing the components of genome editing systems for genome editing in live animals and humans; (iv) in vivo delivery of nuclei acids and proteins such as the components of genome editing system for genome editing in live animals and humans; and (v) in vivo delivery of drugs with or without nuclei acids for drug therapy or gene and drug combination therapy of human diseases including cancer and vascular diseases.

Advantages

The disclosed subject matter has advantages which include, but are not limited to: (i) existing reagents are not as efficient as the invented products in delivering nucleic acids including plasmid DNA, and RNAs including siRNAs in cells to modify expression of specific genes in live subjects (e.g., humans and non-human animals); (ii) the disclosed technology utilizes non-viral delivery with better safety profile; (iii) unlike delivery systems that utilize the adeno-associated virus, there is no limitation on packing capacity of nucleic acids in the disclosed particles; (iv) the disclosed technology can be utilized to deliver genome editing components, e.g., the CRISPR system in a cell-specific manner through cell-specific promoter-controlled expression of editing components, e.g., Cas9, prime editor, base editor, TALEN, Zinc Finger proteins in vivo to achieve cell-specific and transient genome editing and thereby reducing off-target effects; (v) the disclosed technology can be utilized for cell-targeted gene therapy; (vi) the disclosed technology is especially useful for targeting vascular endothelial cells to treat diseases associated/caused by endothelial dysfunction.

Brief Summary of Technology

PLA-PEG nanoparticles made of PEG-b-PLA copolymer are formulated with PEI as a coating to form a novel nanoparticle complex for gene delivery in vivo (e.g., live animals, humans) and also in vitro. The PLA-PEG/PEI complex is then formulated with nucleic acid such as plasmid DNA including its derivatives such as minicircle DNA or nanoplasmid expressing components of genome-editing system such as CRISPR/Cas9, Cas12, Cas13, base editors, prime editing system, Zinc Finger proteins, TALEN, shRNA, siRNA, miRNA, lncRNA, or genes of interest. The plasmid DNA may be formulated at the optimized ratio of 1 g plasmid DNA to 1.2 (0.8-2.4) g PLA35k-PEG5k and 1.5 (1-3) μg PEI25k or succinylated PEI25k, or 45 (15-90) μg PEI600 Da, 2.1 (1-5) μg cPEI with MW cutoff 7 k or 3 (1.5-7.5) μg cPEI with MW cut off 3.5 k per nanoparticle and kept at room temperature for 10 minutes before use. Use of a cell-specific promoter (e.g., endothelial cell-specific promoter CDH5) to control expression of the gene of interest will result in cell-targeted gene therapy with better efficacy and less off-target effects and a better safety profile.

Similarly, the plasmid DNA may be formulated at the optimized ratio of 1 g plasmid DNA to 0.66 (0.5-1.5) g PLGA55k-PEG5k and 1.5 (1-3) μg PEI25k or succineylated PEI25k, or 2.1 (1-5) μg cPEI with MW cutoff 7k or 3 (1.5-7.5) μg cPEI with MW cut off 3.5k per nanoparticle.

Technical Description

PLA-PEG/PEI nanoparticles were prepared by two steps. First, PEG-b-PLA co-polymer was utilized to prepare nanoparticles or micelles by dialysis. The molecular weight of PLA is from 5,000 to 100,000 Da, and the molecular weight of PEG is from 2000 to 20,000 Da. Here we used PEG5000-b-PLA35,000; PEG5,000-b-PLA10,000. Briefly, 20 mg PEG5k-b-PLA35K/PEG5k-b-PLA10k was dissolved in 4 ml acetonitrile. Then 2 ml water was added to the solution and transferred to dialysis tubing with a cutoff of 3500 Da or 7000 Da for dialysis. Two days later, the solution in the dialysis tubing was collected and the concentration of PLA-PEG nanoparticles/micelles were measured by weighing the dried 1 ml micelles solution. Second, the formulated PLA-PEG nanoparticles were mixed with polyethyleneimine (PEI) at various ratios, such as PLA35000-PEG5000: PEI25000=0.4:0.5 (mg/ml), and incubated at 4° C. with shaking for 72 h. Following centrifugation at 19,000×g for 20 min, the pellet was discarded and the supernatant containing the PLA-PEG/PEI nanoparticles was collected. Third, the nanoparticles were mixed with a nucleic acid, such as plasmid DNA, at the optimized ratio of 1 g nucleic acid per nanoparticle containing 0.5-5 g PLA-PEG (e.g., 1.2 g PLA-PEG) and 1-2.5 μg PEI 25K Da (e.g., 1.5 μg PEI 25K Da) or modified PEI25k; or 45 μg (5-90) low MW PEI (e.g., 45 μg PEI600 Da); or 2.1 (1-5) μg cPEI with MW cutoff 7 k or 3 (1.5-7.5) μg cPEI with MW cut off 3.5 k and kept at room temperature for 10 minutes before use. For in vivo animal and human use, the PLA-PEG/PEI nanoparticles loaded with plasmid DNA are intravenously administered for targeting vascular endothelial cells.

Exemplary Problems Solved

The disclosed technology can be utilized for nucleic acid delivery in vivo to animals and humans to manipulate gene expression for functional study and treatment of diseases such as diseases caused by endothelial dysfunction including vascular diseases, pulmonary hypertension, acute respiratory distress syndrome, cancer and cancer metastasis. The lack of safe and efficient delivery tools greatly hinders the application of gene therapy for treatment of human diseases. The disclosed nanoparticle products provide a novel, safer, and highly efficient delivery tool to deliver nucleic acids including plasmid DNA and its derivatives such as minicircle DNA and nanoplasmid, siRNA, miRNA, antisense, lncRNA, and the like for gene therapy of human diseases by manipulating gene expression (e.g., knock-out, knock-in, increased expression, and/or decreased expression). The disclosed technology can be utilized to deliver relatively large nucleic acid (e.g., DNA or RNA that is greater than about 1 kb, 5 kb, 10 kb or greater) in order to express complex systems such as CRISPR systems, base editors, prime editing, TALEN, Zinc, and multiple genes, and use of cell-specific promoter, specifically an endothelial cell-specific promoter, and the like, whereas technology that utilized viral vectors is limited by the package capacity of the vectors.

ILLUSTRATIVE EMBODIMENTS

The following Embodiments are illustrative and should not be interpreted to limit the scope of the claimed subject matter.

Embodiment 1. A composition comprising: (a) a nanoparticle comprising a polyethylene glycol (PEG)-b-poly (D,L-lactide) (PLA) (PEG-b-PLA) copolymer formulated with a cationic polymer, for example as a coating on the nanoparticle; and (b) one or more cargo molecules associated with the nanoparticle, optionally wherein the cargo molecules are negatively charged at physiological pH (e.g., at a pH of about 6-8).

Embodiment 2. The composition of embodiment 1, wherein the cationic polymer is selected from the group consisting of polyethylenimine (PEI), chitosan, poly(2-(dimethylamino)ethyl methacrylate), poly(amino ester) (e.g., a polymer synthesized from an acrylate and an amine via Michael addition), dendrimers, polylysines and other poly (amino acids) such as amino acids that are positively charged at physiological pH (e.g., at a pH of about 6-8 such as 7).

Embodiment 3. The composition of embodiment 1 or 2, wherein the one or more cargo molecules are nucleic acid molecules.

Embodiment 4. The composition of embodiment 3, wherein the one or more nucleic acid molecules is/are DNA and/or RNA.

Embodiment 5. The composition of embodiment 3 or embodiment 4, wherein the one or more nucleic acid molecules is plasmid DNA.

Embodiment 6. The composition of embodiment 3 or embodiment 4, wherein the one or more nucleic acid molecules is minicircle DNA.

Embodiment 7. The composition of embodiment 3 or embodiment 4, wherein the one or more nucleic acid molecules is nanoplasmid DNA.

Embodiment 8. The composition of embodiments 5-7, wherein the plasmid DNA, minicircle DNA, or nanoplasmid expresses a gene, small hairpin RNA, genome editor component(s), CRISPR/Cas9 components, base editors, prime editing components, TALEN system.

Embodiment 9. The composition of embodiment 3 or embodiment 4, wherein the one or more nucleic acid molecules is a small interfering RNA (siRNA), miRNA, long non-coding RNA (lncRNA), antisense RNA, coding RNA.

Embodiment 10. The composition of embodiment 1, wherein the one or more cargo molecules are small molecules.

Embodiment 11. The composition of any one of embodiments 1-10, wherein the PEI is a modified or unmodified large molecular weight PEI (e.g., a MW>10 kDa or a MW>25 kDa), optionally wherein the modification is succinylation.

Embodiment 12. The composition of any one of embodiments 1-11, wherein the ratio of cargo molecule to PLA-PEG to PEI is about 1 μg:0.8-5 μg:1-100 μg.

Embodiment 13. The composition of any one of embodiments 1-12, wherein the PEI is PEI25 kDa.

Embodiment 14. The composition of embodiment 12, wherein the ratio of cargo molecule to PLA-PEG to PEI is 1 μg plasmid DNA:0.8-5 μg (e.g. 1.2 μg) PLA-PEG: 1-2.5 μg (e.g. 1.5 μg) PEI25k.

Embodiment 15. The composition of any one of embodiments 1-9, wherein the PEI is a modified or unmodified low molecular weight PEI.

Embodiment 16. The composition of embodiment 15, wherein the ratio of cargo molecule to PLA-PEG to PEI is 1 μg plasmid DNA:0.8-2.4 μg (e.g. 1.2 μg) PLA-PEG: 5-100 μg low MW PEI400, 600, 800, 1200, 1800 (e.g. 45 μg PEI600 Da).

Embodiment 17. The composition of embodiment 15, wherein the modification is acetylation.

Embodiment 18. The composition of any one of embodiments 1-17, wherein the PEI is modified or unmodified crosslinked low molecular weight PEI polyplex.

Embodiment 19. The composition of embodiment 18, wherein the crosslinker is a diacrylate, a disulfide, a disimine, a carbamate, an amide, or a ketal.

Embodiment 20. The composition of any one of embodiments 1-9, wherein the PEI is diacrylate-crosslinked PEI800 (cPEI800), cPEI400, cPEI600, cPEI1200, cPEI1800, and optionally wherein the ratio of cargo to PLGA-PEG to cPEI is 1 ug plasmid DNA:0.8-2.4 μg (e.g., 1.2 μg) PLA-PEG: 1.5-5 μg (e.g. 2.1 μg cPEI800 with MW cutoff 7 k or 3 μg cPEI800 with MW cutoff 3.5 k.

Embodiment 21. The composition of embodiment 18, wherein the PEI is PEI 400, 600, 800, 1200, 1800 Da.

Embodiment 22. A method of delivering one or more cargo molecules to a cell, which comprises contacting the cell with the composition of any one of embodiments 1-21, whereby the cargo molecule is delivered to the cell.

Embodiment 23. The method of embodiment 22, wherein the one or more cargo molecules are nucleic acid molecules.

Embodiment 24. The method of embodiment 22, wherein the method is performed in vitro or in vivo.

Embodiment 25. The method of embodiment one of embodiments 22-24, wherein the cell is an endothelial cell or a cancer cell.

Embodiment 26. The method of any one of embodiments 22-25, wherein the nucleic acid molecule comprises a nucleic acid sequence that is operatively linked to a ubiquitous promoter, a cell-specific promoter, or a tissue-specific promoter.

Embodiment 27. The method of embodiment 26, wherein the ubiquitous promoter is the CAG promoter.

Embodiment 28. The method of embodiment 26, wherein the nucleic acid molecule comprises a nucleic acid sequence that is operatively linked to an endothelial cell-specific promoter.

Embodiment 29. A composition comprising: (a) a nanoparticle comprising a poly(lactic acid-co-glycolic acid) (PLGA)-b-polyethylene glycol (PEG) copolymer (PEG-b-PLGA) (i.e., PLGA-PEG nanoparticles) formulated with a cationic polymer (e.g., as a coating) and (b) one or more cargo molecules associated with the nanoparticle, optionally wherein the cargo molecules are negatively charged at physiological pH (e.g., a pH of about 6-8 such as 7).

Embodiment 30. The composition of embodiment 29, wherein the cationic polymer is polyethylenimine (PEI), chitosan, is poly(2-(dimethylamino)ethyl methacrylate), poly(aminoester)s such as polymers formed by reacting an acrylate and an amino via Michael addition, dendrimers, polylysines and other poly(amino acids) such as amino acids that are positively charged at physiological pH (e.g., pH of 6-8 such as 7).

Embodiment 31. The composition of embodiment 30, wherein the PEI is crosslinked PEI (cPEI) of a small molecular weight PEI (e.g., 400, 600, 800, 1200, 1800 Da), wherein the crosslinker is a diacrylate, a disimine, a carbamate, an amide, or a ketal.

Embodiment 32. The composition of any one of embodiments 29-31, wherein the PEI is diacrylate-crosslinked PEI800 (cPEI800), cPEI400, cPEI600, cPEI1200, cPEI1800, optionally wherein the ratio of cargo to PLGA-PEG to cPEI is 1 ug plasmid DNA:0.5-2 μg (e.g., 0.66 μg) PLGA-PEG:1-10 μg (e.g. 2.1 μg cPEI800 dialysed with MW cut off 7 k or 3.0 μg cPEI800 dialysed with MW cut off 3.5 k.

EXAMPLES

The following Examples are illustrative and should not be utilized to limit the scope of the claimed subject matter.

BACKGROUND

The cardiovascular endothelium is a monolayer of endothelial cells lining the luminal surface of all blood vessels. Among its vital functions are regulation of vascular permeability and retention of blood cells in the circulation.

(See Cines et al., Blood 91, 3527-3561 (1998)). Because of its permeability properties, the endothelial-cell layer permits free exchange of small crystalloid and nutrient molecules across vessel walls, but is highly restrictive to protein, thus enabling formation of an oncotic pressure gradient, which counter-balances the hydrostatic pressure generated by the pumping action of the heart to achieve tissue-fluid balance at physiological vascular pressures. (See Mehta, D. and Malik, A. B., *Physiol Rev,* 86: 279-367 (2006)). The endothelial layer also plays a key role in vasomotor regulation in all vascular beds and is critically involved in the regulation of immune and coagulation responses with precise localization to the area of need. (See Munoz-Chapuli, *Evol. Dev.,* 7: 351-358 (2005)). The endothelium is responsible for the antithrombotic surface of normal blood vessels, and provides a nearly frictionless conduit for blood flow, thus minimizing the energy required to propel the blood. (See Monahan-Earley et al., *Thromb. Haemost.,* 11 Suppl 1: 46-66 (2013)). Under adverse conditions (as for example, infection, tissue necrosis, immune reactions, or hypercholesterolemia) endothelial cells are activated, leading to inflammation and endothelial barrier disruption (increased vascular permeability, edema fluid formation, release of proinflammatory cytokines, and leukocyte extravasation). (See Ware., L. B. and Matthay, M. A., *N. Engl. J. Med.,* 342: 1334-1349 (2000)).

Endothelial dysfunction figures prominently in the etiology of atherosclerosis, the pathological process underlying the major cardiovascular diseases (myocardial infarction, stroke, coronary artery disease), hypertension, pulmonary hypertension, sepsis, acute respiratory distress syndrome (ARDS), extreme limb ischemia, restenosis. The ability to genetically modify the endothelia of the cardiopulmonary vascular system has been challenging thus far considering the lack of a delivery system capable of targeting endothelia other than the liver for genome editing and/or expression of gene of interest.

The experiments described below demonstrate that nanoparticle-mediated delivery of an all-in-one-CRISPR plasmid DNA expressing Cas9 under the control of the human CDH5 promoter (endothelial cell-specific) results in highly efficient genome editing specifically in endothelial cells (ECs) of the cardiopulmonary vascular system including heart, lung, aorta and peripheral vessels in adult mice, which leads to disruption of gene expression and a phenotype mimicking that of genetic knockout mice. The experiments described below also demonstrate that nanoparticle delivery of plasmid DNA results in increased gene expression in vascular endothelial cells.

Example 1—Preparation of PLA-PEG/PEI Nanoparticles and Use Thereof for Delivery of DNA In Vitro and In Vivo FIG. 1 is a schematic diagram which illustrates the preparation of PEI-coated PLA-PEG (PLA-PEG/PEI) nanoparticles using a dialysis method. To prepare the PLA-PEG/PEI nanoparticles, 20 mg $PLA_{35k\ Da}$-b-$PEG_{5k\ Da}$ or $PLA_{10k}$-b-$PEG_{5k}$ copolymer was dissolved in 4 ml acetonitrile then 2 ml water was added to the solution and the solution was transferred to dialysis tubing (cutoff 3500 Da). After dialysis for 2 days, the solution was collected and incubated with branched PEI25K Da, low MW PEI (400, 600,800,1200,1800,2000 Da), or crosslinked low MW PEI (cPEI) for 3 days at 4° C. to generate PLA-PEG/PEI nanoparticles.

Figure 2:
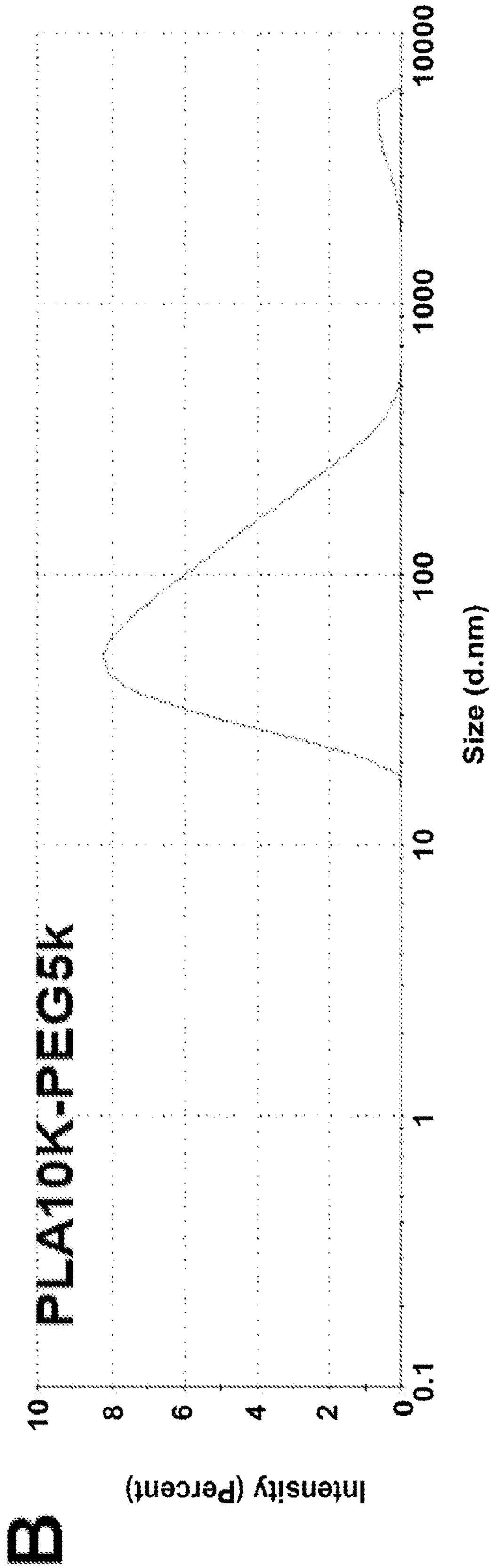
FIG. 2 are graphs which illustrate the size distribution of PLA10k Da.-PEG5 k Da. nanoparticles and PEI25 k Da.-coated PLA-PEG nanoparticles formulated at different weight ratios (A and B).

FIG. 2A and FIG. 2B are graphs which illustrate the Zeta potential and size distribution of PLA-PEG nanoparticles and PEI-coated PLA-PEG nanoparticles. $PLA_{10k}$-$PEG_{5k}$ nanoparticles were mixed with $PEI_{25k}$ (molecular weight) at various weight ratios and incubated for 72 hours at room temperature and then collected for determination of size distribution and zeta potential.

Figure 3:
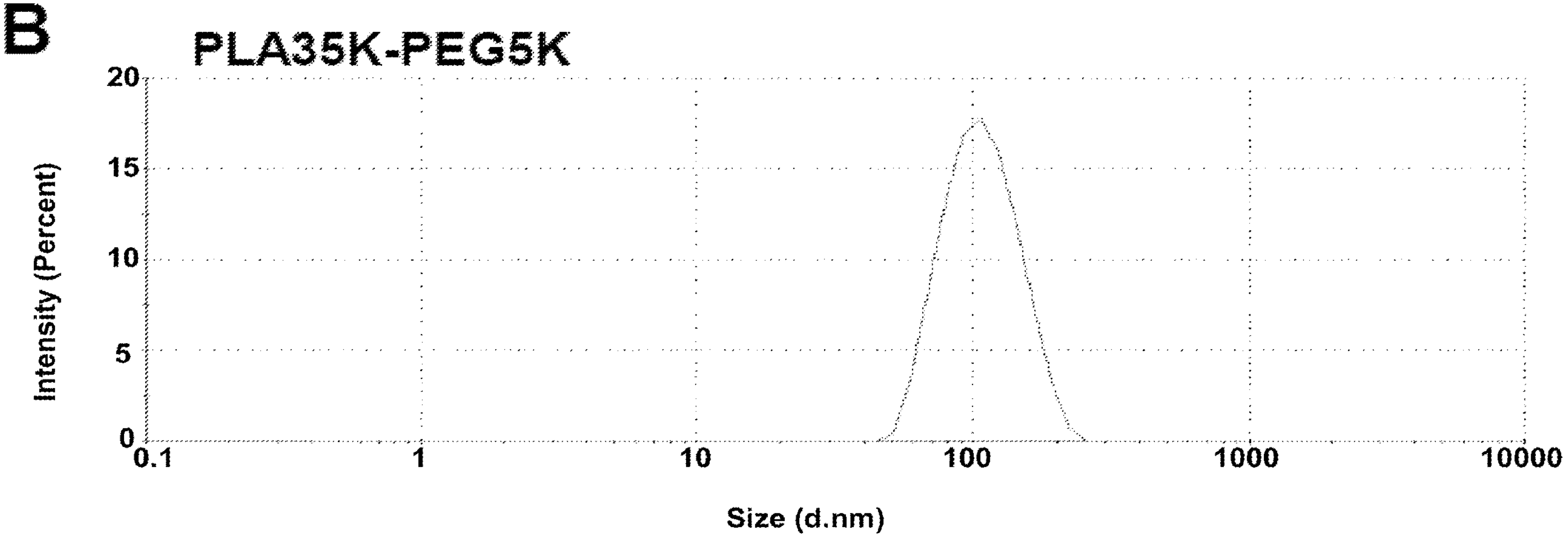
FIG. 3 are graphs which illustrate size and Zeta potential of PLA35k-PEG5k nanoparticles and PEI 25k-coated PLA35k-PEG5k nanoparticles formulated at different weight ratios (A and B).
Figure 3:
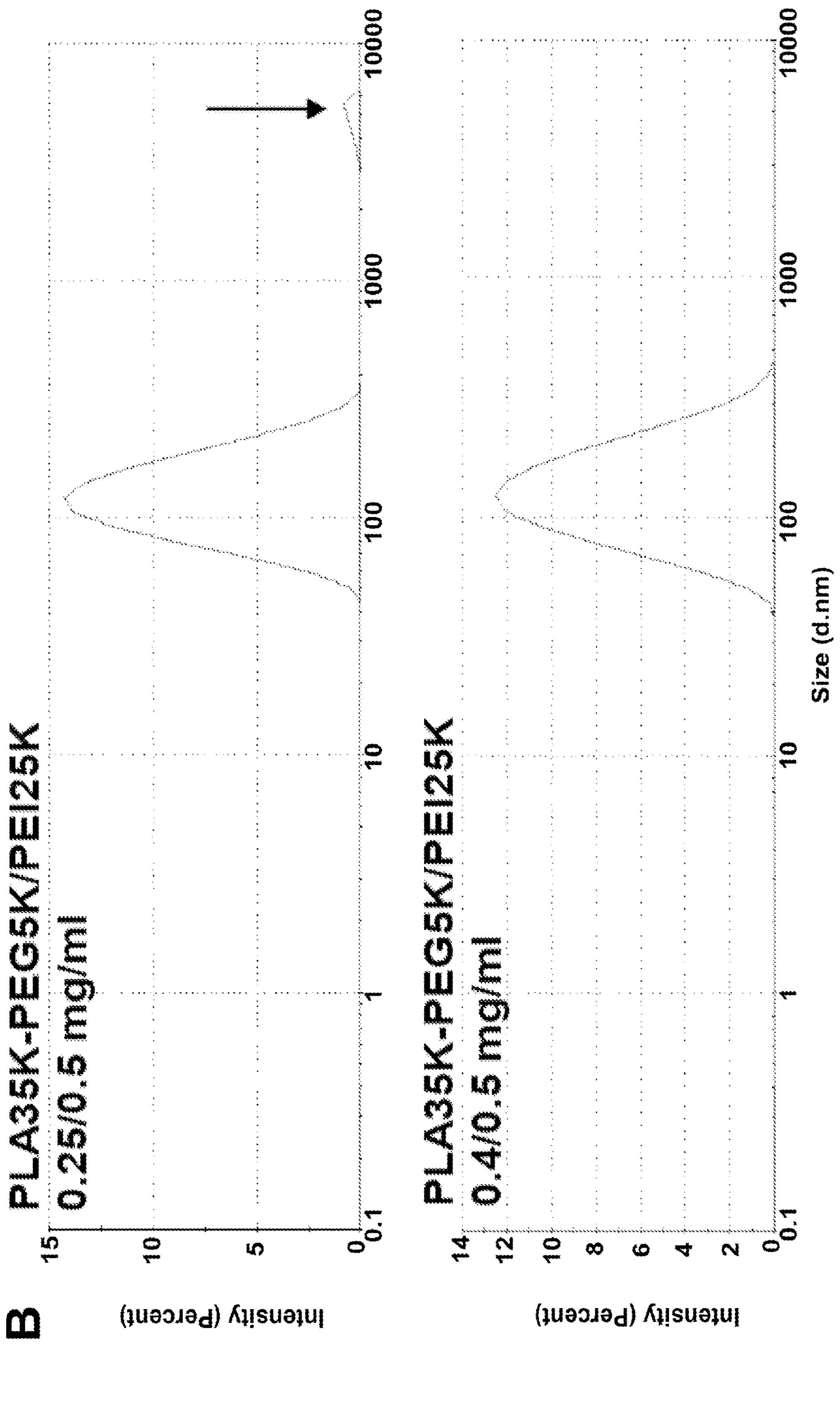

FIG. 3A and FIG. 3B are graphs which illustrate the Zeta potential and size distribution of PLA35k-PEG5k nanoparticles and PEI 25k-coated PLA35k-PEG5k nanoparticles prepared as described.

Figure 4:
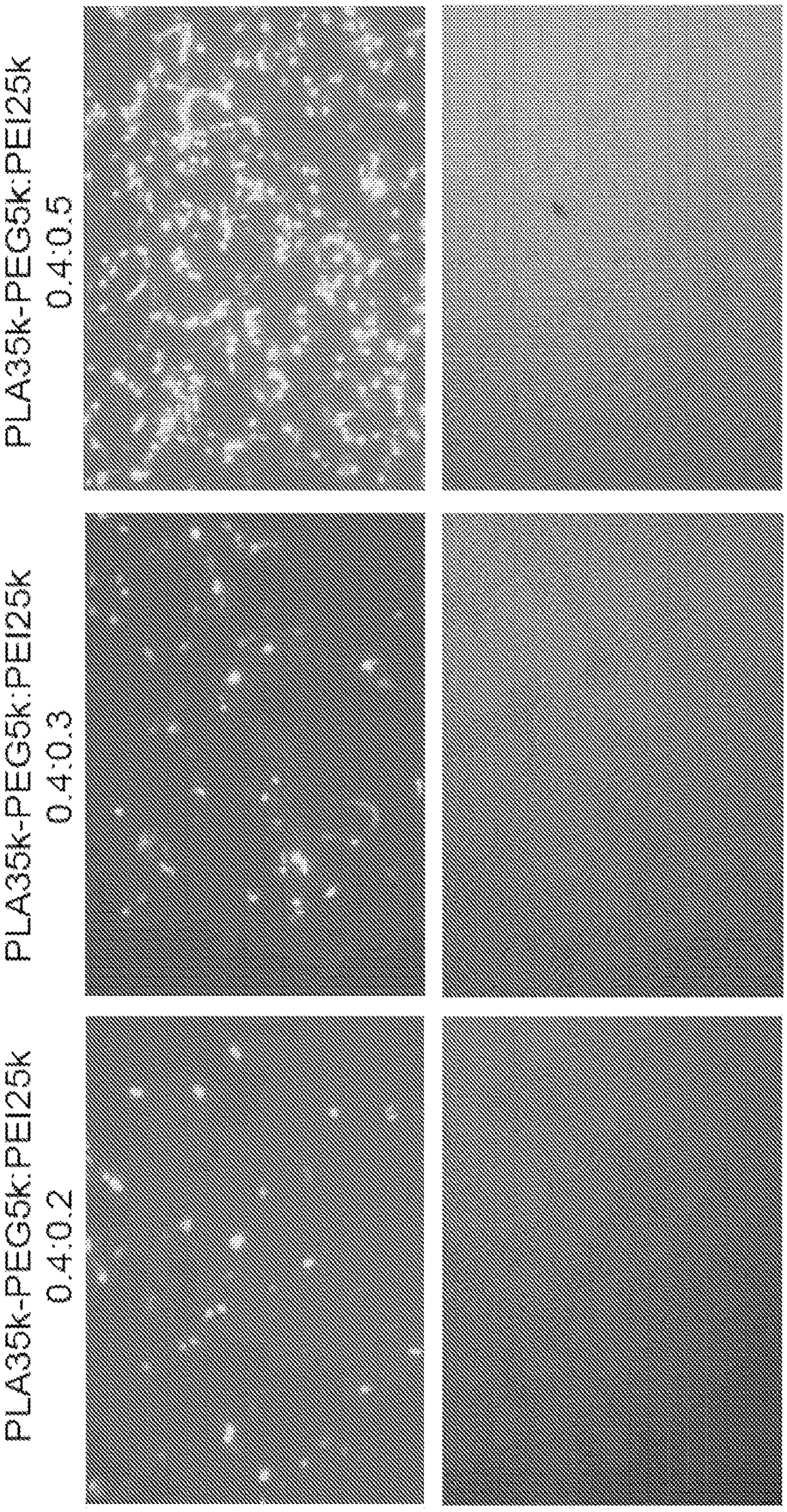
FIG. 4 is a series of fluorescent microscopy images and phase contrast images (black and white) which illustrate the transfection efficiency and toxicity of $PLA_{35k}$-$PEG_{5k}$/PEI25k nanoparticle delivery of plasmid DNA expressing GFP (green). The ratio of 0.4 mg PLA-PEG:0.5 mg PEI25k gave the best results.
Figure 4:
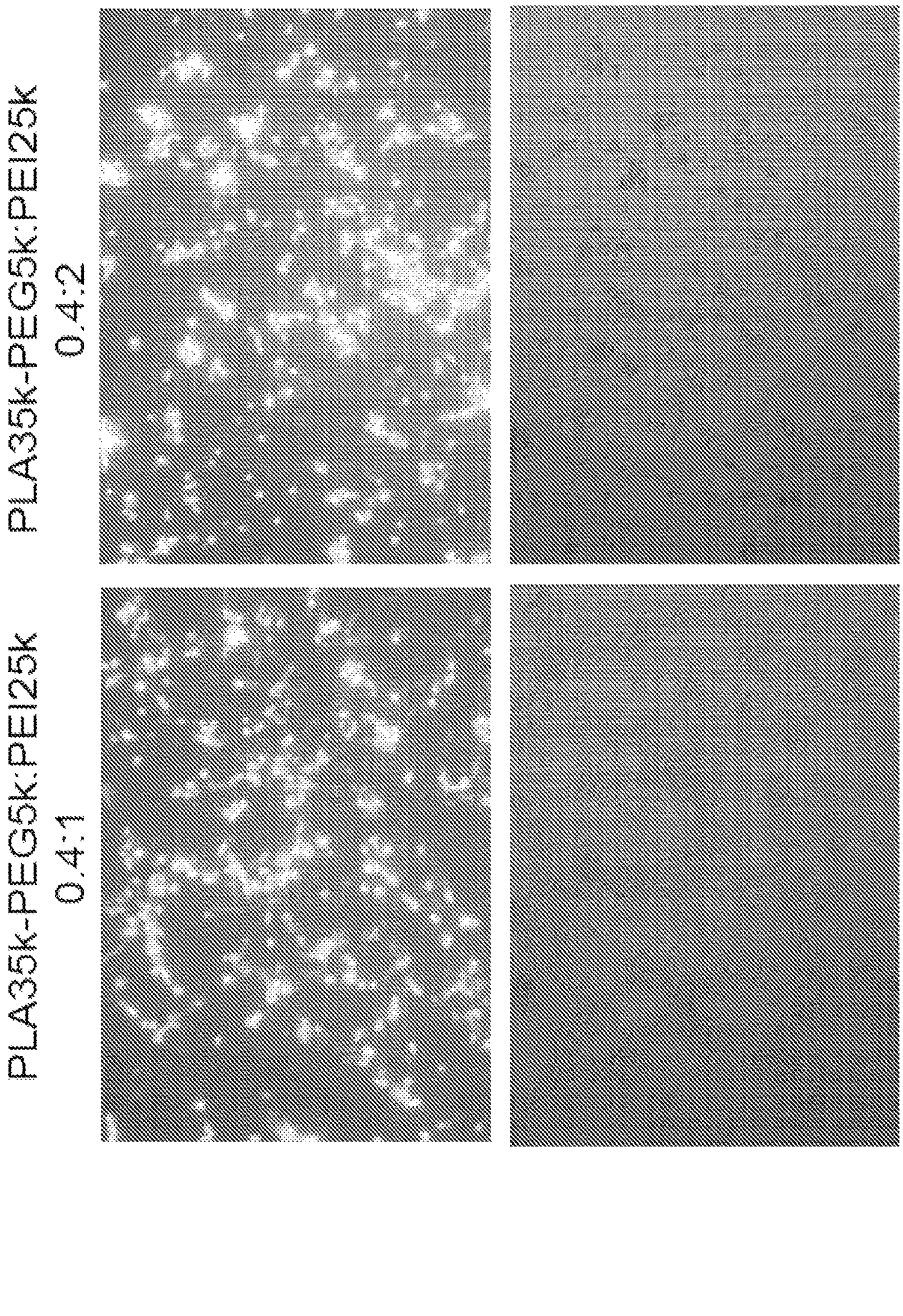

FIG. 4 is a series of fluorescent microscopy images and phase contrast images (black and white) took at 72 h post-nanoparticle delivery of DNA, which illustrate the transfection efficiency and toxicity of $PLA_{35k}$-$PEG_{5k}$/PEI25k nanoparticle delivery of plasmid DNA expressing GFP (green). The ratio of 0.4 mg PLA-PEG:0.5 mg PEI25k gave the best results.

Figure 5:
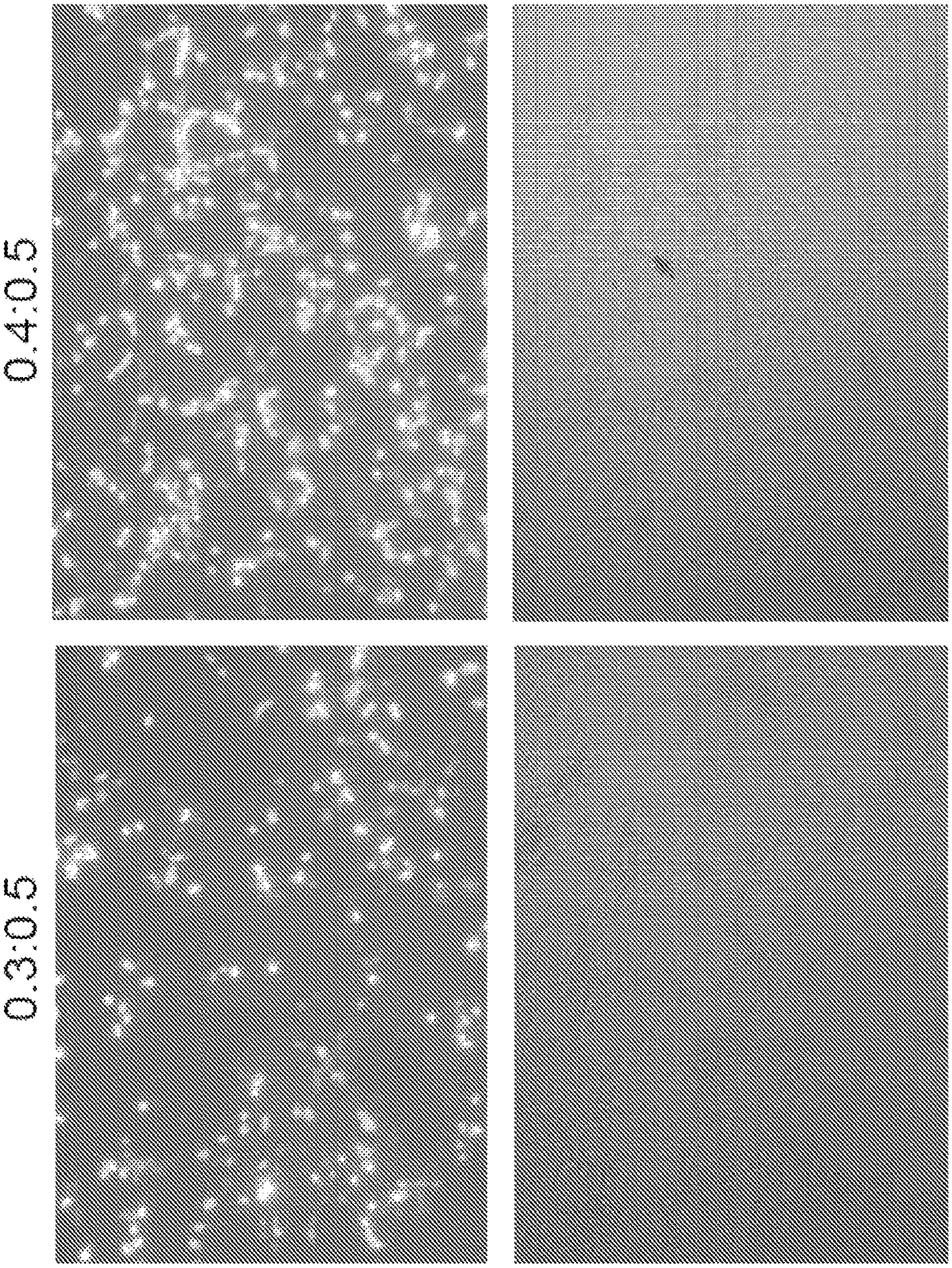
FIG. 5 is a series of fluorescent microscopy images and phase contrast images (black and white) which illustrate the transfection efficiency and toxicity of $PLA_{35k}$-$PEG_{5k}$/PEI25k-plasmid DNA nanoparticles. The ratio of 0.4 mg PLA-PEG:0.5 mg PEI25k gave the best results.
Figure 5:
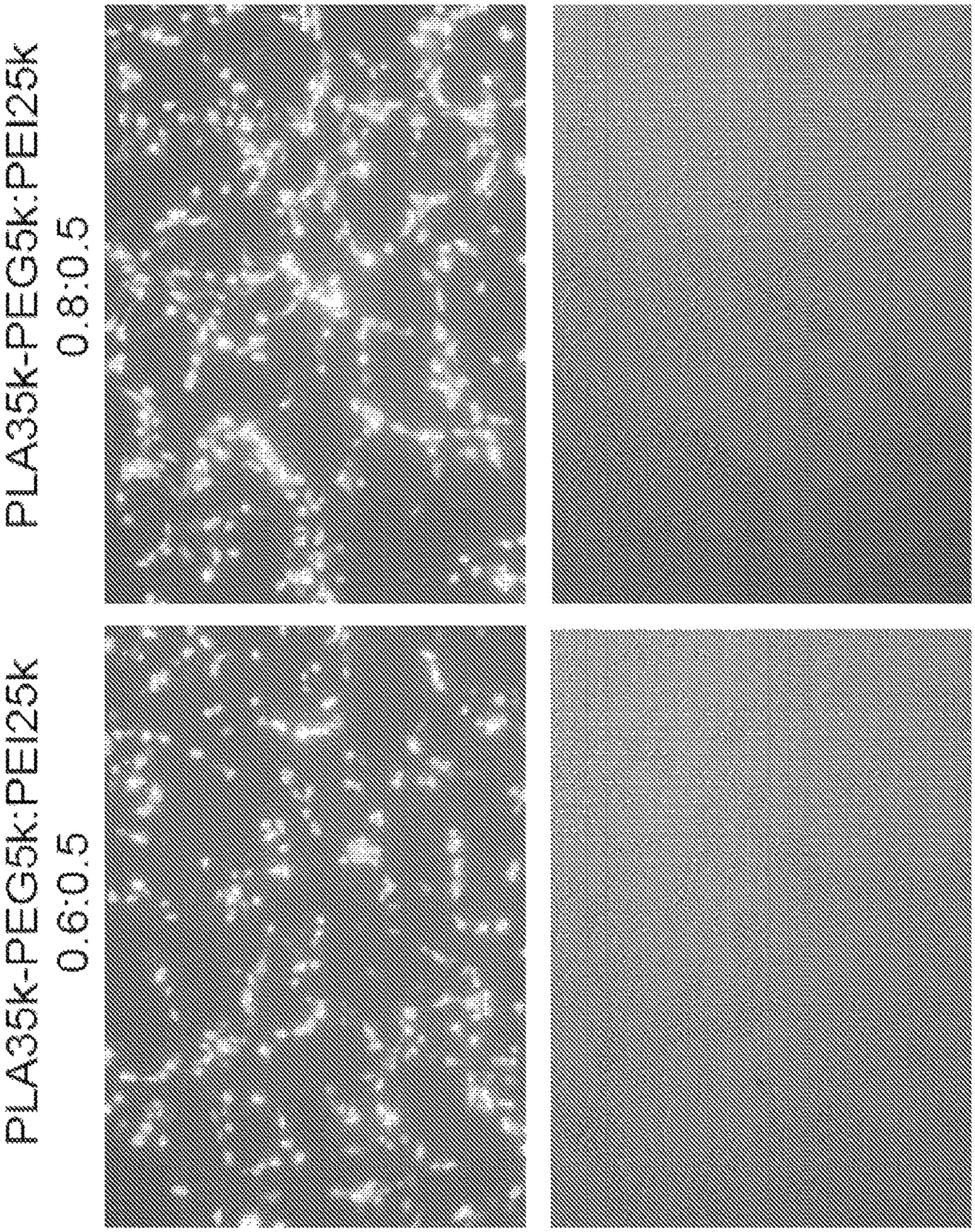
Figure 6:
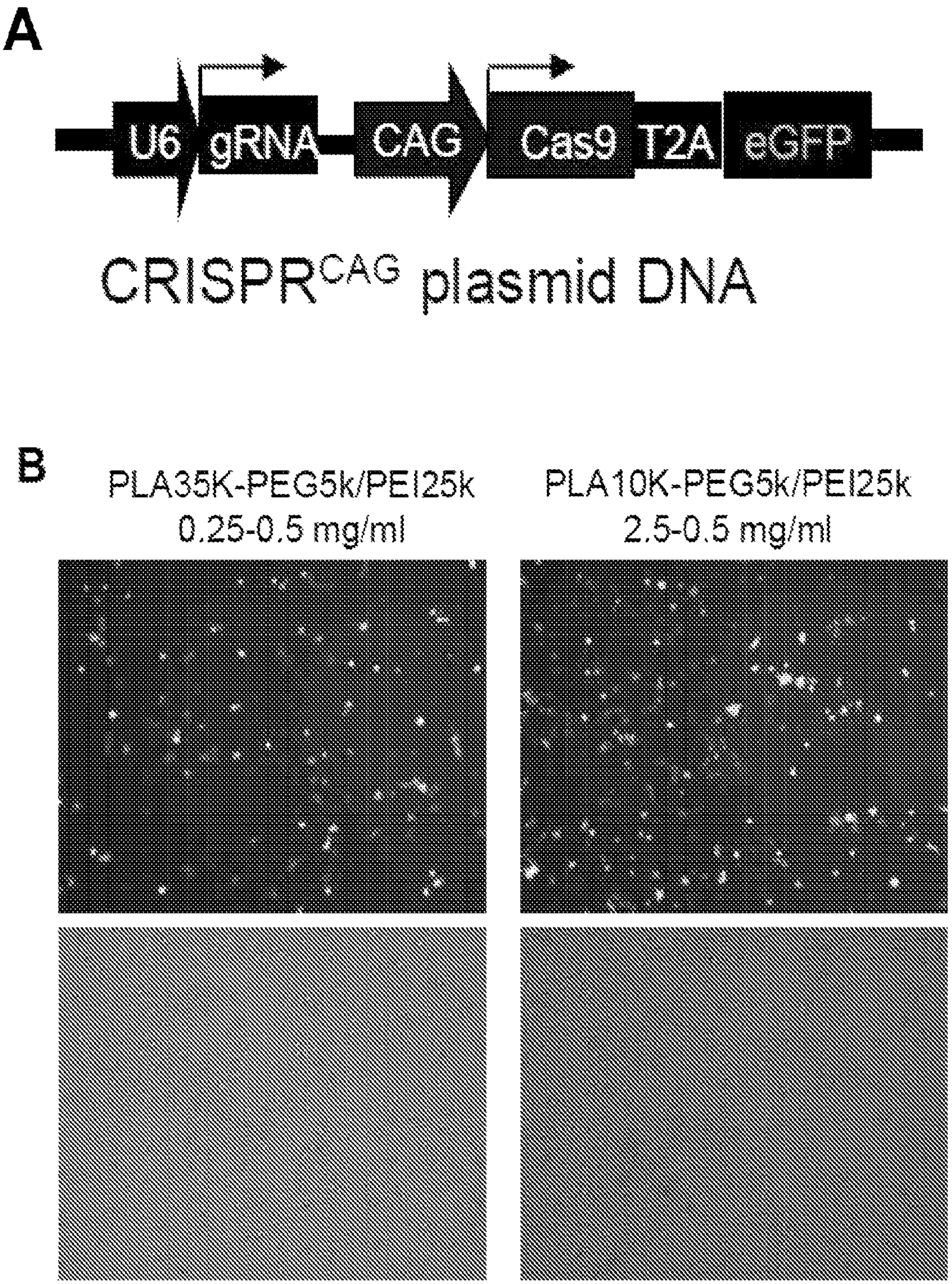
FIG. 6 consists of a diagram illustrates the plasmid DNA expressing CRISPR Cas9 under the control of CAG (or CDH5 promoter for in vivo targeting endothelial cells) promoter and gRNA by U6 promoter (A); a series of fluorescent microscopy images which illustrate the transfection efficiency of PLA-PEG/PEI nanoparticle:plasmid DNA in vitro (Hepa1c1c7 cells) (B); a graph showing more than 70% knockdown of p110γPI3K gene expression in nanoparticle/CRISPR plasmid DNA expressing Cas9 and Pik3cg-specific gRNA but not by PLA35k-PEG5k/PEI25k formulated at 0.25 mg/ml:0.5 mg/ml ratio, demonstrating the importance of specific ratio for formulation (C).
Figure 6:
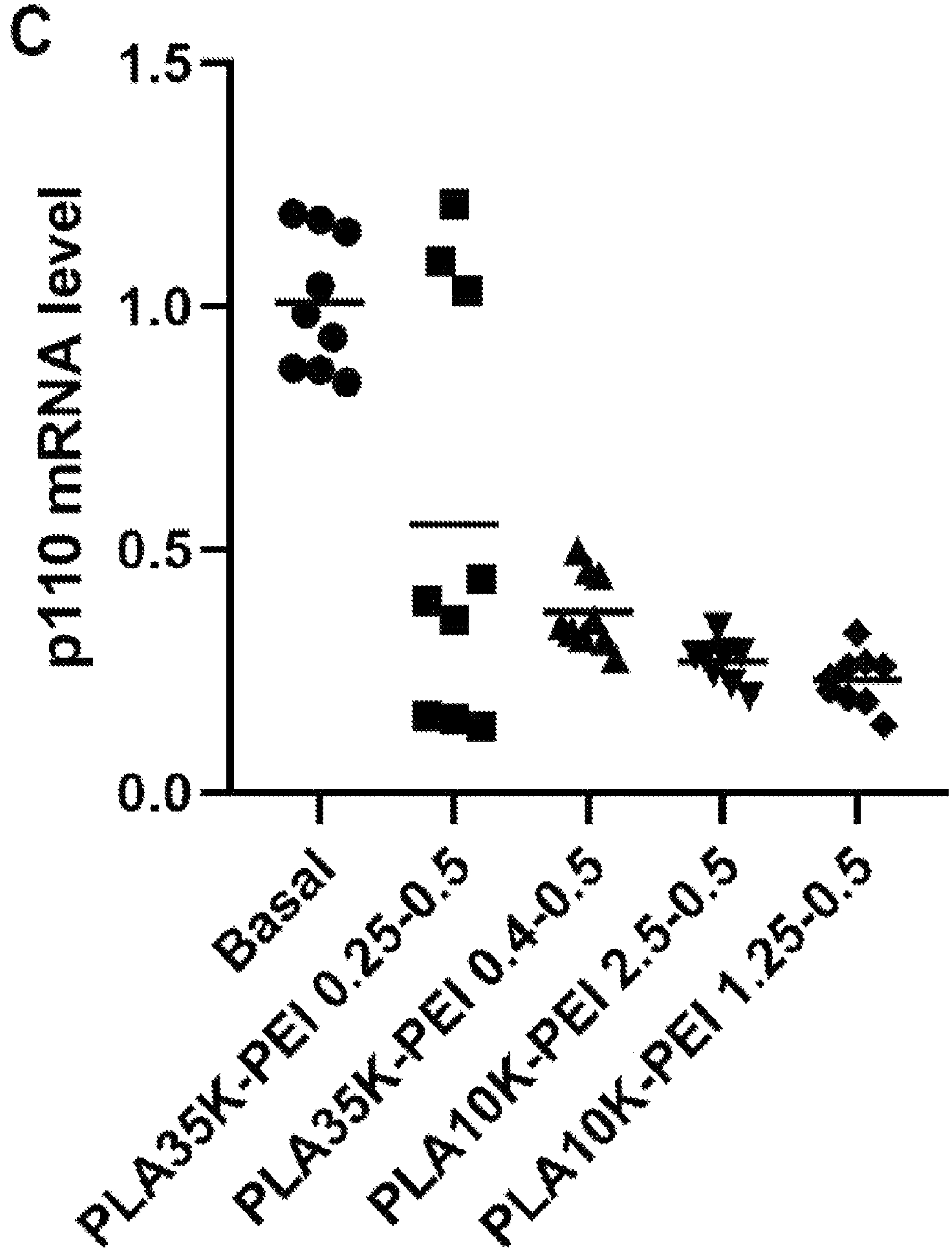

FIG. 5 is a series of fluorescent microscopy images and phase contrast images (black and white) which illustrate the transfection efficiency and toxicity of $PLA_{35k}$-$PEG_{5k}$/PEI25k-plasmid DNA nanoparticles. The ratio of 0.4 mg PLA-PEG:0.5 mg PEI25k gave the best result FIG. 6A is a diagram that illustrates the plasmid DNA expressing CRISPR Cas9 under the control of the CAG promoter (or the CDH5 promoter for in vivo targeting endothelial cells) and gRNA by the U6 promoter. FIG. 6B is a series of fluorescent microscopy images and phase contrast images (black and white) which illustrate the transfection efficiency of PLA-PEG/PEI nanoparticles/plasmid DNA in vitro in Hepa1c1c7 cells. In the experiments, 12 μl of nanoparticles were mixed with 3 g of CRISPR plasmid DNA and added to Hepa-1c1c7 cells for 48 hours. Expression of GFP was detected using fluorescent microscopy. FIG. 6C is a graph showing more than 70% knockdown of p110γPI3K gene expression after administering a nanoparticle containing CRISPR plasmid DNA expressing Cas9 and Pik3cg-specific gRNA. The p110γPI3K gRNA target sequence is 5'-ACCGTACCACGACAGTGCGC-3'(SEQ ID NO: 3).

Figure 7:
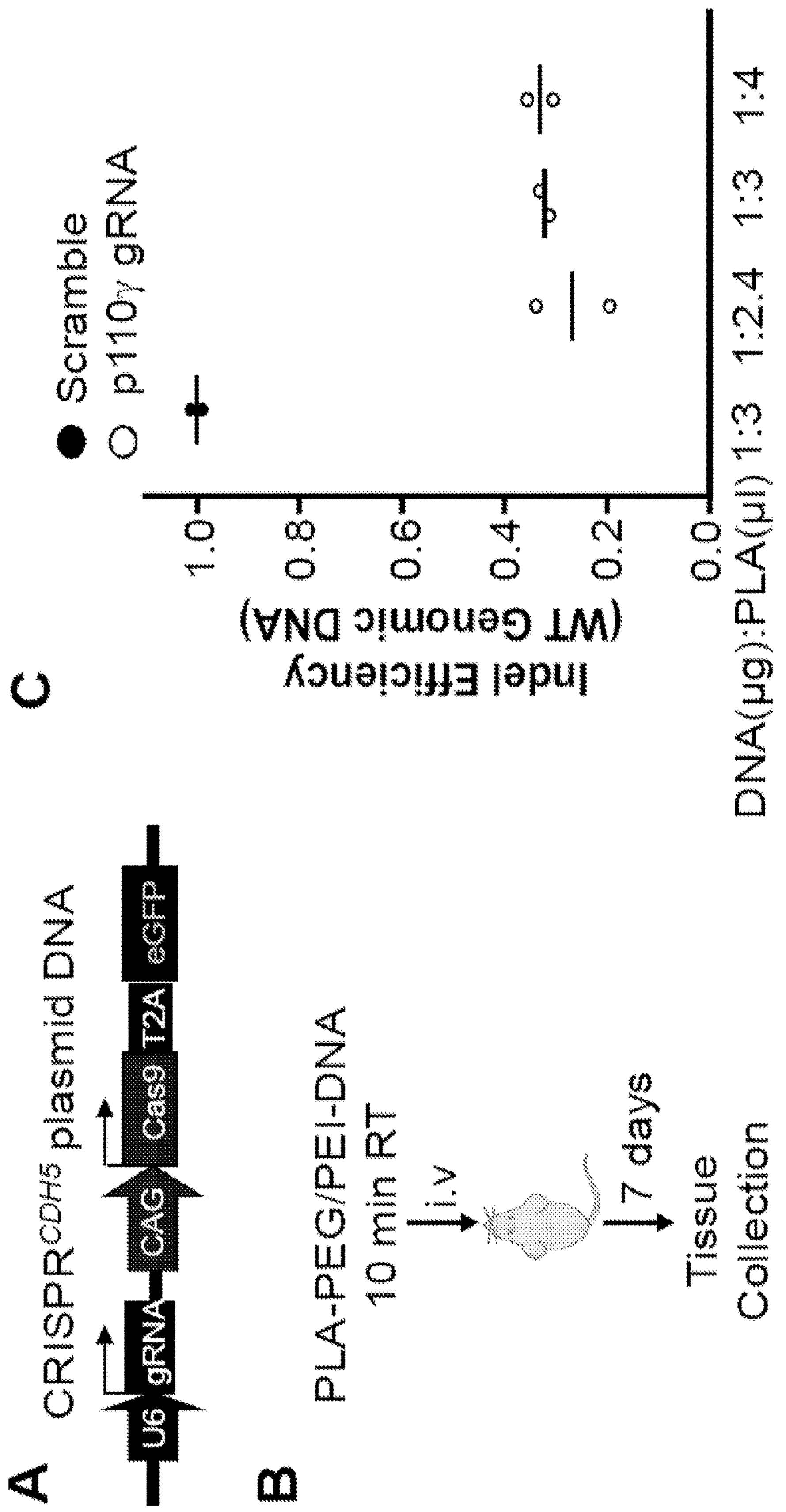
FIG. 7 consists of a diagram which illustrates the plasmid DNA expressing CRISPR Cas9 under the control of CDH5 promoter for in vivo targeting endothelial cells and gRNA by U6 promoter (A); a graph which illustrates the process of nanoparticle-mediated delivery of the CRISPR system to adult mice (B); a graph which illustrates a quantitative PCR analysis showing 60% genome Indel (Insertion/deletion) efficiency in freshly isolated lung ECs ($CD31^+$) in mice treated with $CRISPR^{CDH5}$/p110γ gRNA plasmid DNA-loaded PLA35k-PEG5k/PEI25k nanoparticles but not in mice treated with $CRISPR^{CDH5}$/scrambled RNA plasmid (C); a graph which illustrates an Evans blue-conjugated albumin (EBA) extravasation assay in mouse lungs demonstrating persistent lung vascular leaking in mice treated with $CRISPR^{CDH5}$/p110γ gRNA plasmid DNA-loaded PLA-PEG/PEI nanoparticles at 72 h post-sepsis challenge (D). The nanoparticle:plasmid DNA at 1:3 ratio shows the best result. A graph which illustrates myeloperoxidase activity indicative of neutrophil sequestration in mouse lungs (E).
Figure 7:
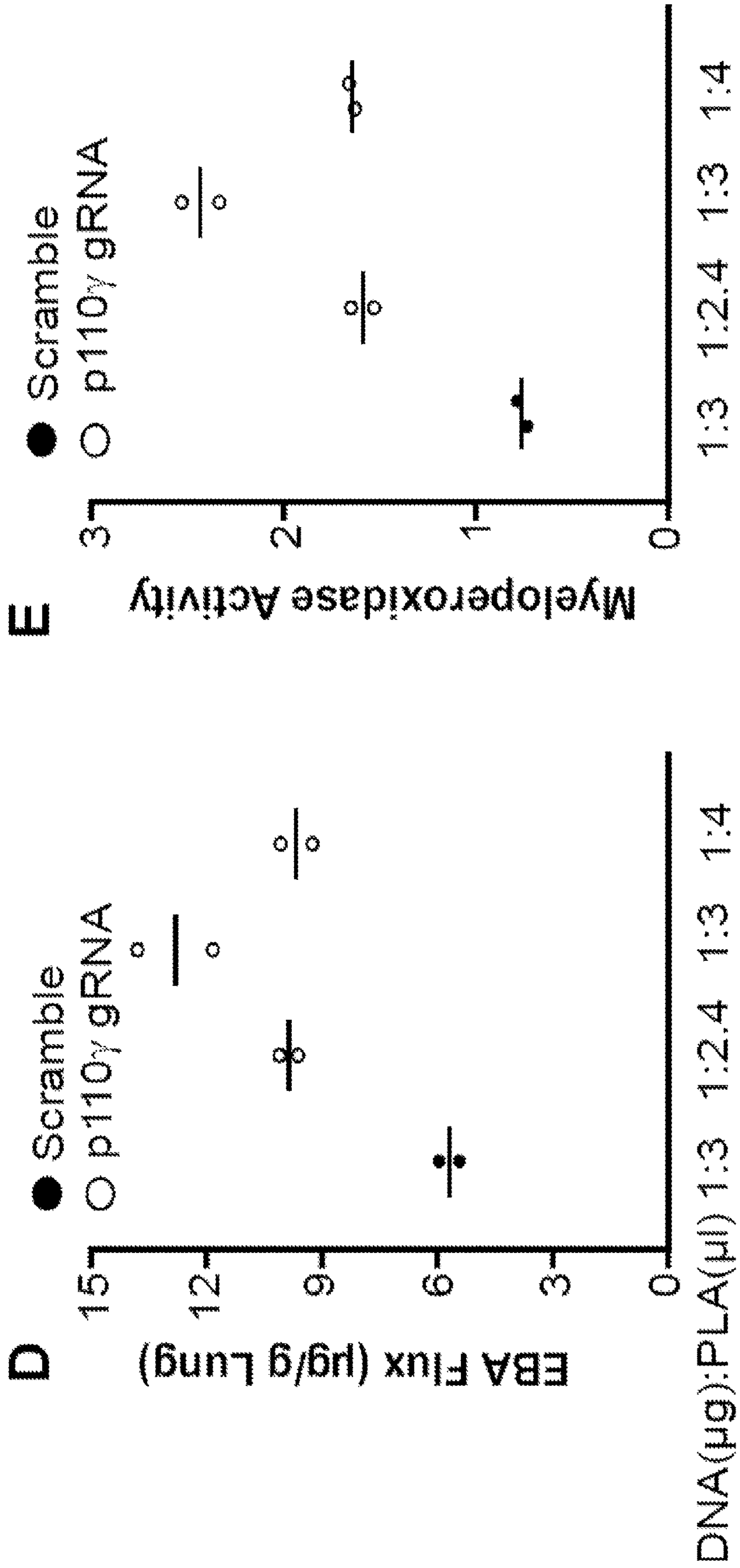

FIG. 7 7A is a diagram which illustrates the plasmid DNA expressing CRISPR Cas9 under the control of CDH5 promoter for in vivo targeting endothelial cells and gRNA by U6 promoter. FIG. 7B is a graph which illustrates the process of nanoparticle-mediated delivery of the CRISPR system to adult mice. FIG. 7C is a graph which illustrates a quantitative PCR analysis showing 60% genome Indel (Insertion/deletion) efficiency in freshly isolated lung ECs (CD31') in mice treated with $CRISPR^{CDH5}$/p110γ gRNA plasmid DNA-loaded PLA35k-PEG5k/PEI25k (PLA) nanoparticles but not in mice treated with $CRISPR^{CDH5}$/scrambled RNA plasmid. FIG. 7D is a graph which illustrates an Evans blue-conjugated albumin (EBA) extravasation assay in mouse lungs demonstrating persistent lung vascular leaking in mice treated with $CRISPR^{CDH5}$/p110γ gRNA plasmid DNA-loaded PLA-PEG/PEI nanoparticles at 72 h post-sepsis challenge. The nanoparticle:plasmid DNA at 1:3 ratio shows the best result. FIG. 7E is a graph which illustrates myeloperoxidase activity indicative of neutrophil sequestration in mouse lungs. 7 days post-administration of PLA-PEG/PEI:DNA mixture, lung tissues were collected for endothelial cell isolation by magnetic beads. Genomic DNA was then isolated for quantitative PCR analysis with the following primers, 5'-TTGAACCGTACCACGACAGTG-3' (SEQ ID NO:1); 5'-ACCAGAACAAGAAGTGACCGAT (SEQ ID NO:2).

Example 2—Preparation of PLA-PEG/cPEI Nanoparticles and Use Thereof for Transfection of DNA In Vitro and In Vivo Although large molecular weight PEIs are potentially toxic due to their aggregation and difficulty degrading, low molecular weight PEIs (e.g. MW~400, 600, 800, 1200, 1800-2000 Da) are well tolerated. Low MW PEIs, however, exhibit low binding capacity for nucleic acids. (See Godbey et al., *J Biomed Mater Res.,* 45: 268-275 (1999); Breunig et al., *Proc Natl Acad Sci USA,* 104: 14454-14459 (2007)). Low molecular weight PEIs, e.g. PEI800 Da were cross-linked by diacrylate bonds to form a large molecular complex (cPEI) and dialyzed with different MW cut off (1 k, 2 k, 3.5 k and 7 k MW). The cross-linked PEIs (cPEIs) then were formulated with PLA-PEG nanoparticle for gene delivery (e.g., via cPEI-coating of the PLA-PEG nanoparticles). Similar transfection efficiency with either PEI25k or cPEI800 was achieved in formulation with either PLA-PEG nanoparticles or PLGA-PEG nanoparticles. This example demonstrates highly efficient gene delivery by novel formulation of biodegradable crosslinked low molecular weight PEI.

Figure 8:
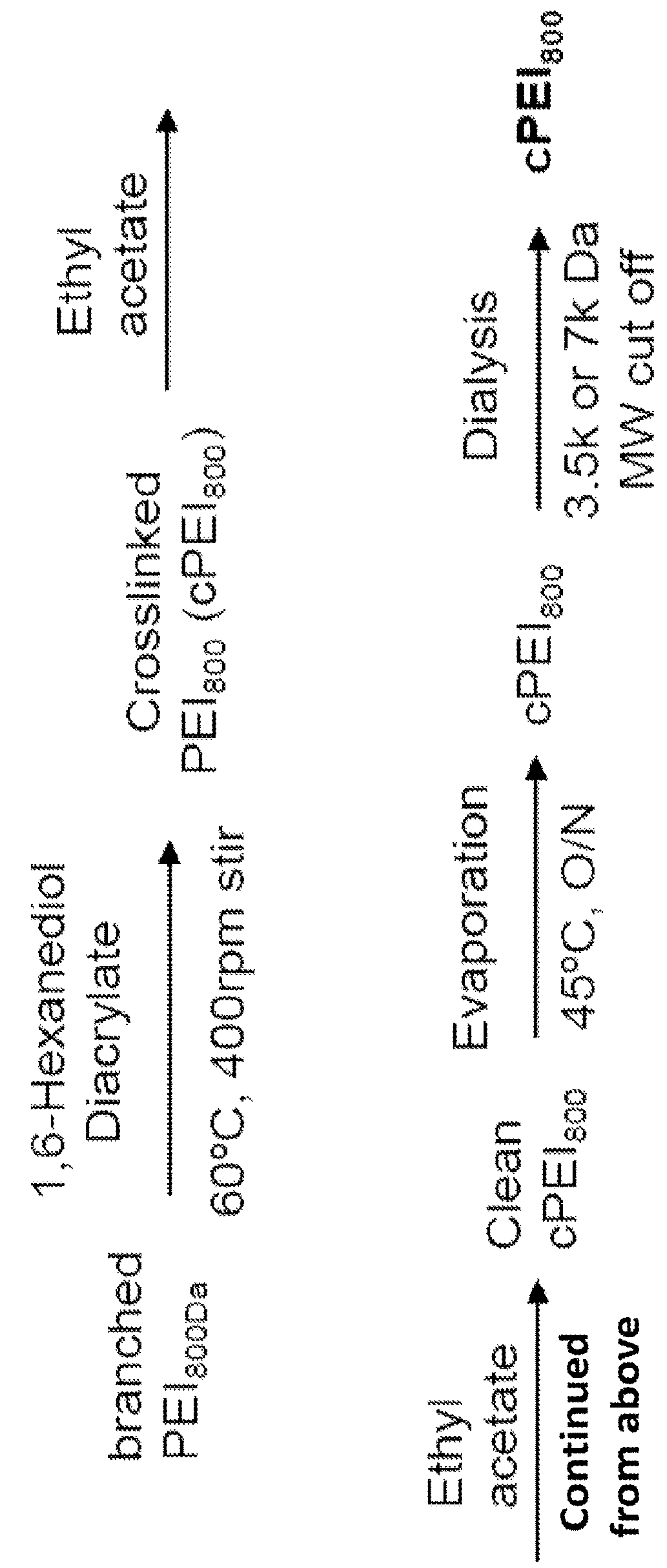
FIG. 8 is a diagram showing generation of biodegradable diacrylate-crosslinked PEI800 (cPEI800).

FIG. 8 is a diagram showing generation of biodegradable diacrylate-crosslinked PEI800 (cPEI800). To prepare cPEI800, 600 μL of 1,6-Hexanediol Diacrylate was added dropwise to 2 g of a branched $PEI_{800\ Da}$ solution at 60° C. with 400 rpm magnetic stirring. The solution was incubated for 3 days, then washed with ethyl acetate 3 times. The solution was collected from a separating funnel and evaporated to remove trace ethyl acetate in the solution via a rotary evaporator at 45° C. for overnight. The solution then was dialyzed with a 2K MW cutoff.

Figure 9:
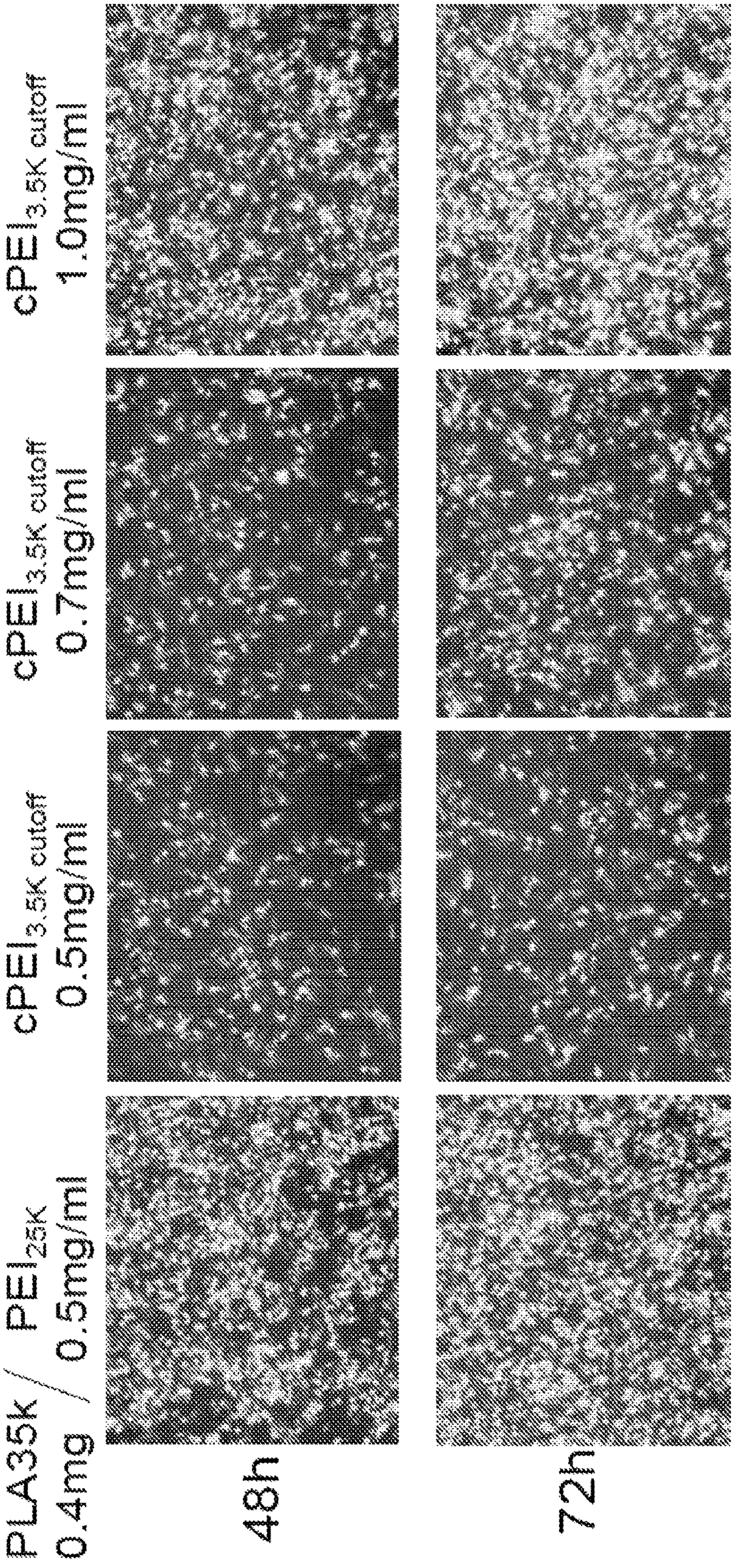
FIG. 9 is a series of fluorescent microscopy images which illustrate the transfection efficiency and toxicity of $PLA_{35k}$-$PEG_{5k}$/cPEI800 (MW cut off 3.5 k Da during dialysis) nanoparticles in delivering plasmid DNA expressing GFP (green) compared to $PLA_{35k}$-$PEG_{5k}$/PEI25k nanoparticles. Red-framed micrograhs show highly toxic nanoparticles. The ratios of 0.4 mg PLA35k-PEK5k:1.0-1.5 mg cPEI are the best.
Figure 9:
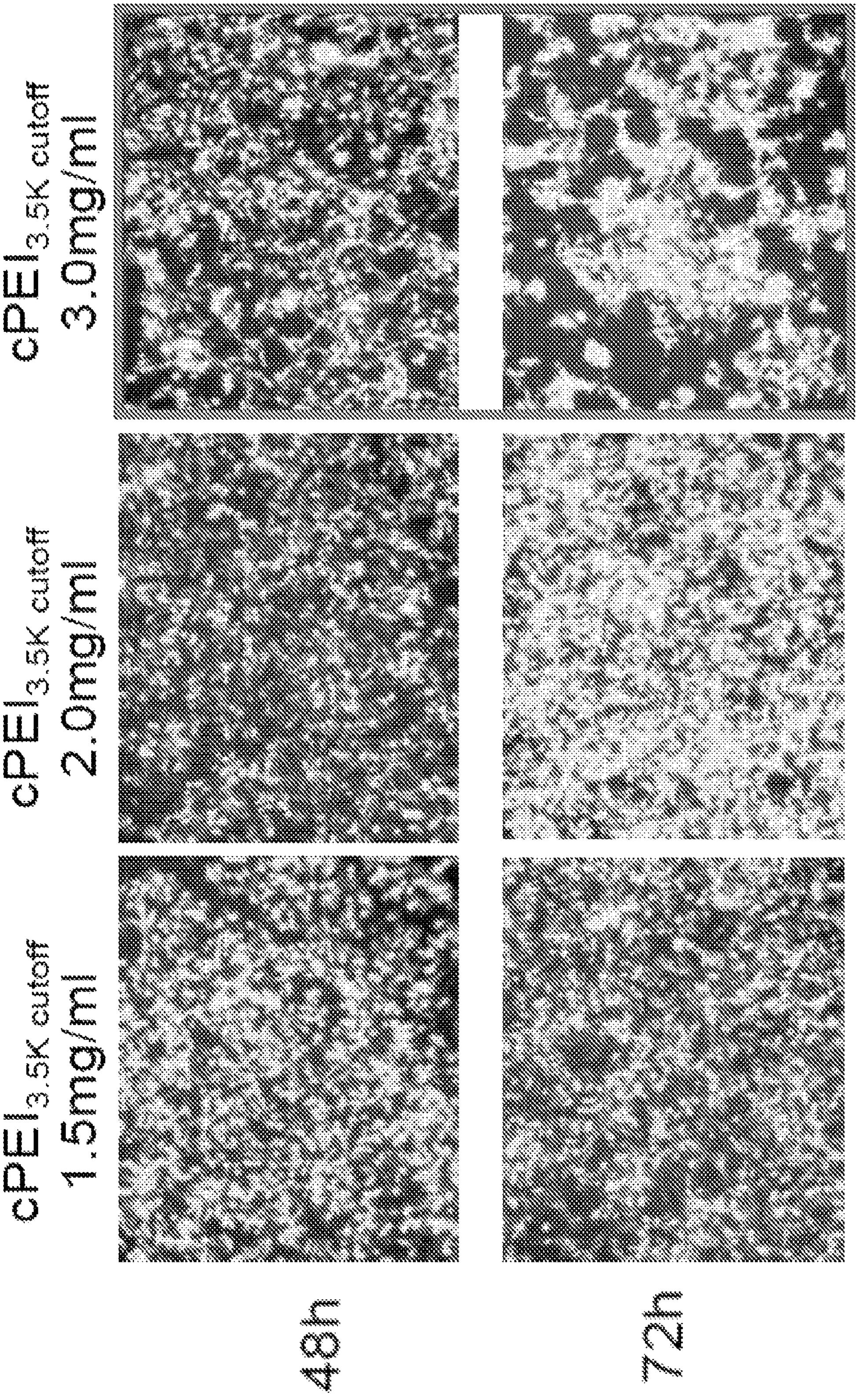

FIG. 9 is a series of fluorescent microscopy images which illustrate the transfection efficiency and toxicity of $PLA_{35k}$-$PEG_{5k}$/cPEI800 (MW cut off 3.5 k Da during dialysis) nanoparticles in delivering plasmid DNA expressing eGFP (green) compared to PLA35k-PEG5k/PEI25k nanoparticles. Red-framed micrograhs show highly toxic nanoparticles. The ratios of 0.4 mg PLA35k-PEK5k:1.0-1.5 mg cPEI are the best.

Figure 10:
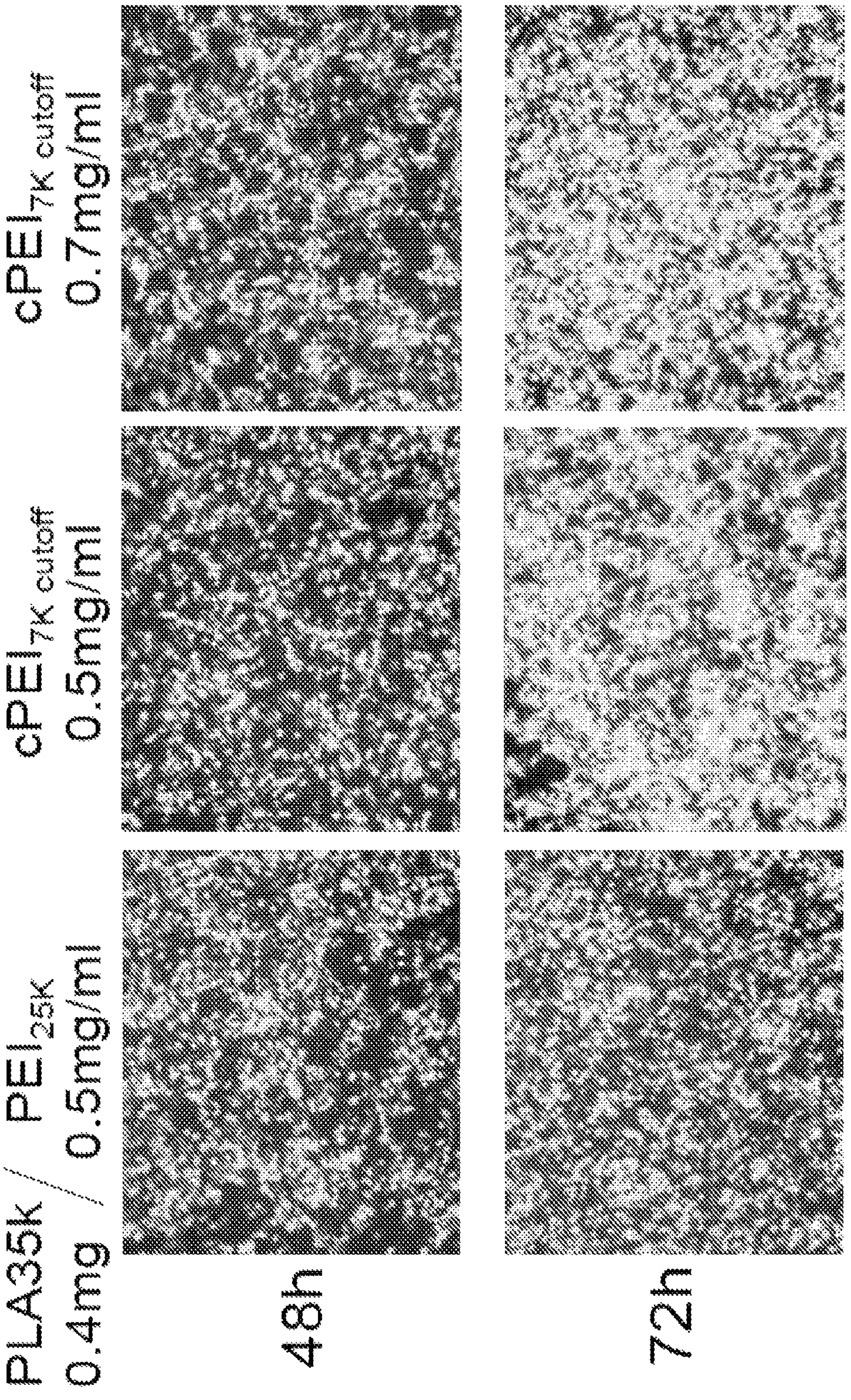
FIG. 10 is a series of fluorescent microscopy images which illustrate the transfection efficiency and toxicity of $PLA_{35k}$-$PEG_{5k}$/cPEI800 (MW cut off 7 k Da during dialysis) nanoparticles compared to $PLA_{35k}$-$PEG_{5k}$/PEI25k nanoparticles. The ratios of 0.4 mg PLA35k-PEK5k:0.7-1.2 mg cPEI are the best.
Figure 10:
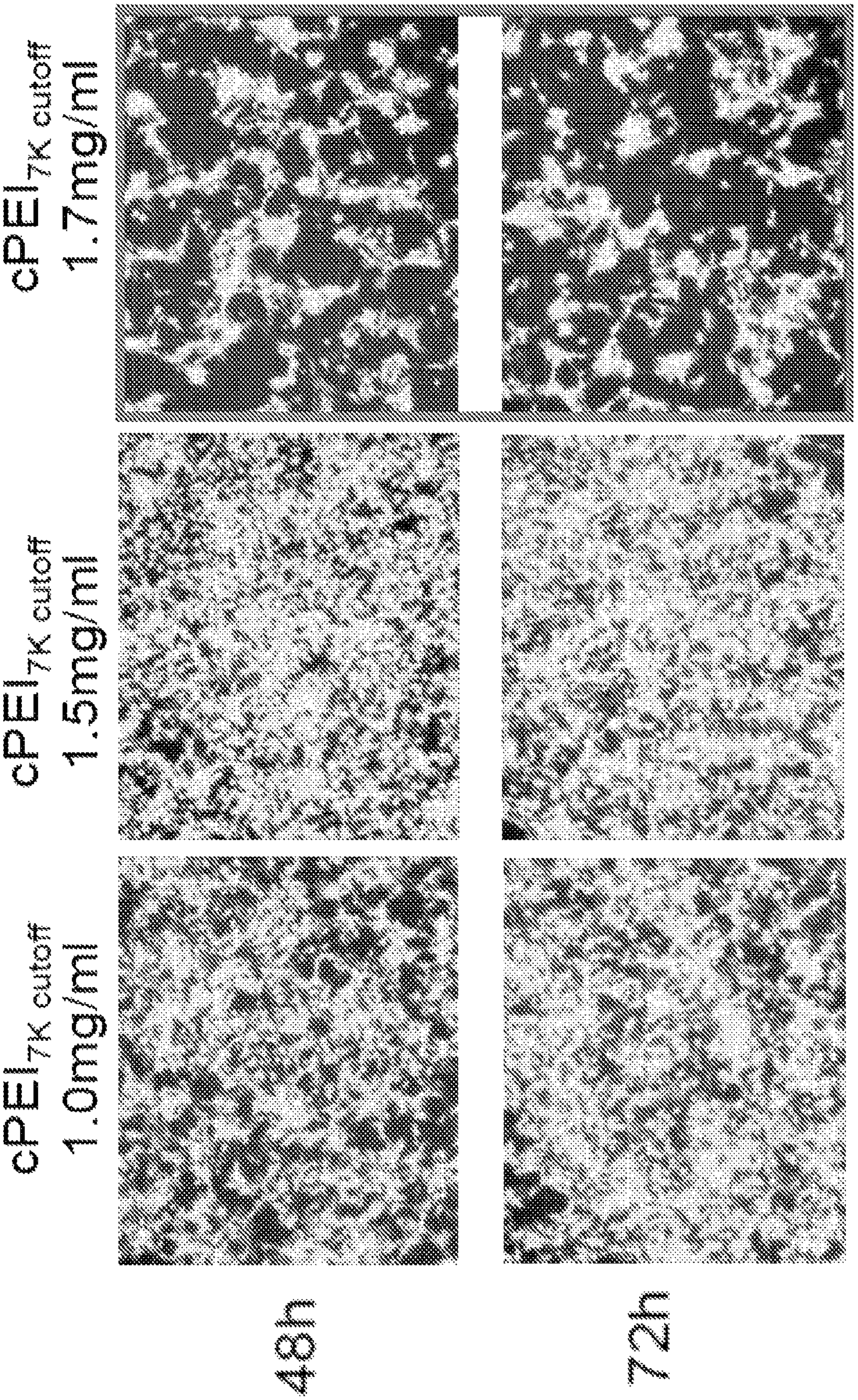

FIG. 10 is a series of fluorescent microscopy images which illustrate the transfection efficiency and toxicity of $PLA_{35k}$-$PEG_{5k}$/cPEI800 (MW cutoff 7 k Da during dialysis) nanoparticles compared to $PLA_{35k}$-$PEG_{5k}$/PEI25k nanoparticles. The ratios of 0.4 mg PLA35k-PEK5k:0.7-1.2 mg cPEI are the best.

Figure 11:
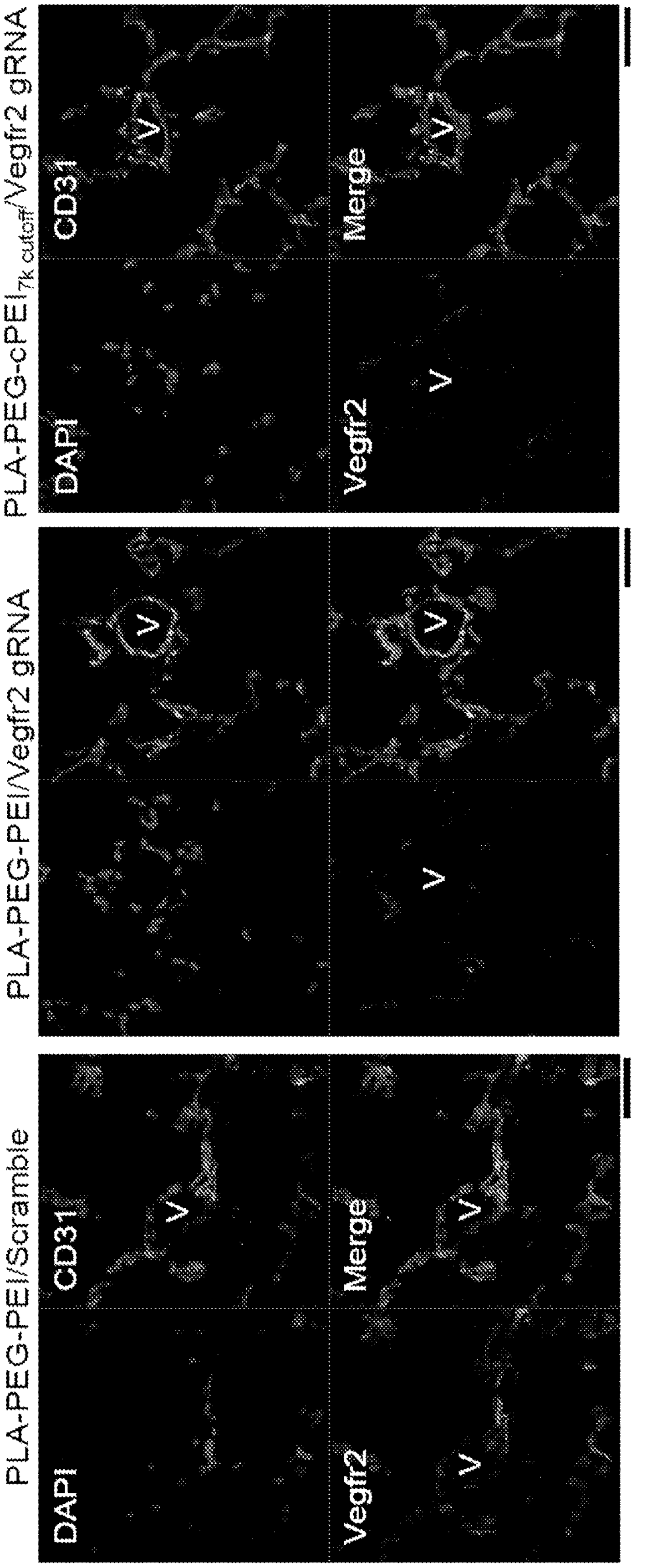
FIG. 11 is a series of fluorescent microscopy images which illustrate the knockout (genome editing) efficiency of $CRISPR^{CDH5}$ plasmid expressing Vegfr2 gRNA delivered by either PLA35k-PEG5k/PEI25k nanoparticles or PLA35-PEG5k/cPEI800 (7k cut off) in mouse lung vascular ECs. V=vessel.

FIG. 11 is a series of fluorescent microscopy images which illustrate the knockout (genome editing) efficiency of $CRISPR^{CDH5}$ plasmid expressing Vegfr2 gRNA delivered by either PLA35k-PEG5k/PEI25k nanoparticles or PLA35-PEG5k/cPEI800 (7 k Da cutoff) in mouse lung vascular ECs. V=vessel. 7 days after nanoparticle:plasmid DNA administration, lung tissues were collected for cryosection and immunostaining with anti-VEGFR2 (red) and CD31 (green, marker for ECs). Nuclei were counterstained with DAPI. Scale bar, 50 μm. The Vegfr2 gRNA target sequence is 5'-CAACCCTTCAGATTACTTGC-3'(SEQ ID NO: 4).

Figure 12:
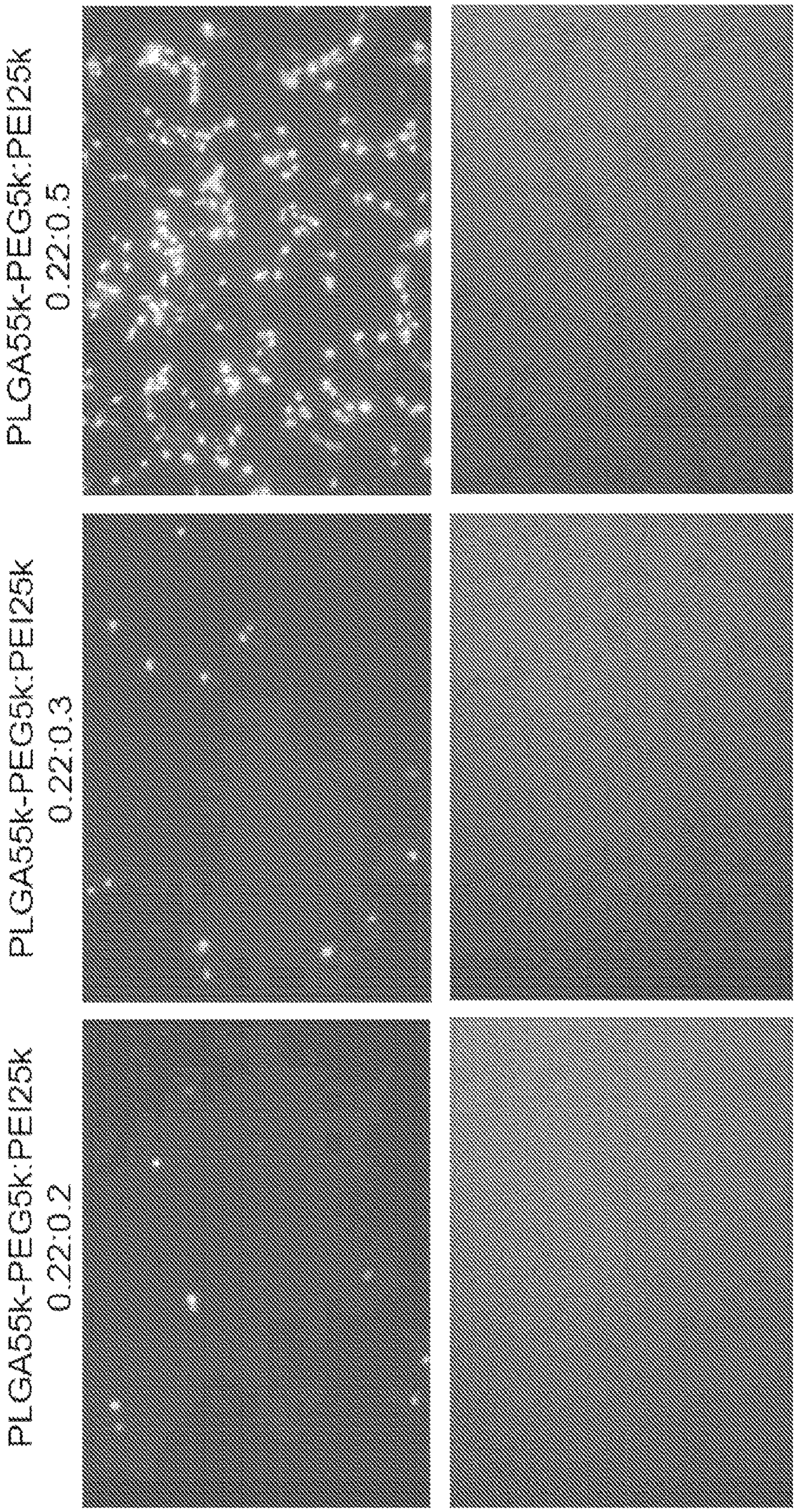
FIG. 12 is a series of fluorescent microscopy images and phase contrast images (black and white) which illustrate the transfection efficiency and toxicity of $PLGA_{55k}$-$PEG_{5k}$/PEI25k nanoparticle delivery of plasmid DNA expressing GFP (green). The ratio of 0.22 mg PLGA-PEG:0.5-1 mg PEI25k gave the best results. PLGA=poly(Lactic Acid-co-Glycolic Acid).
Figure 12:
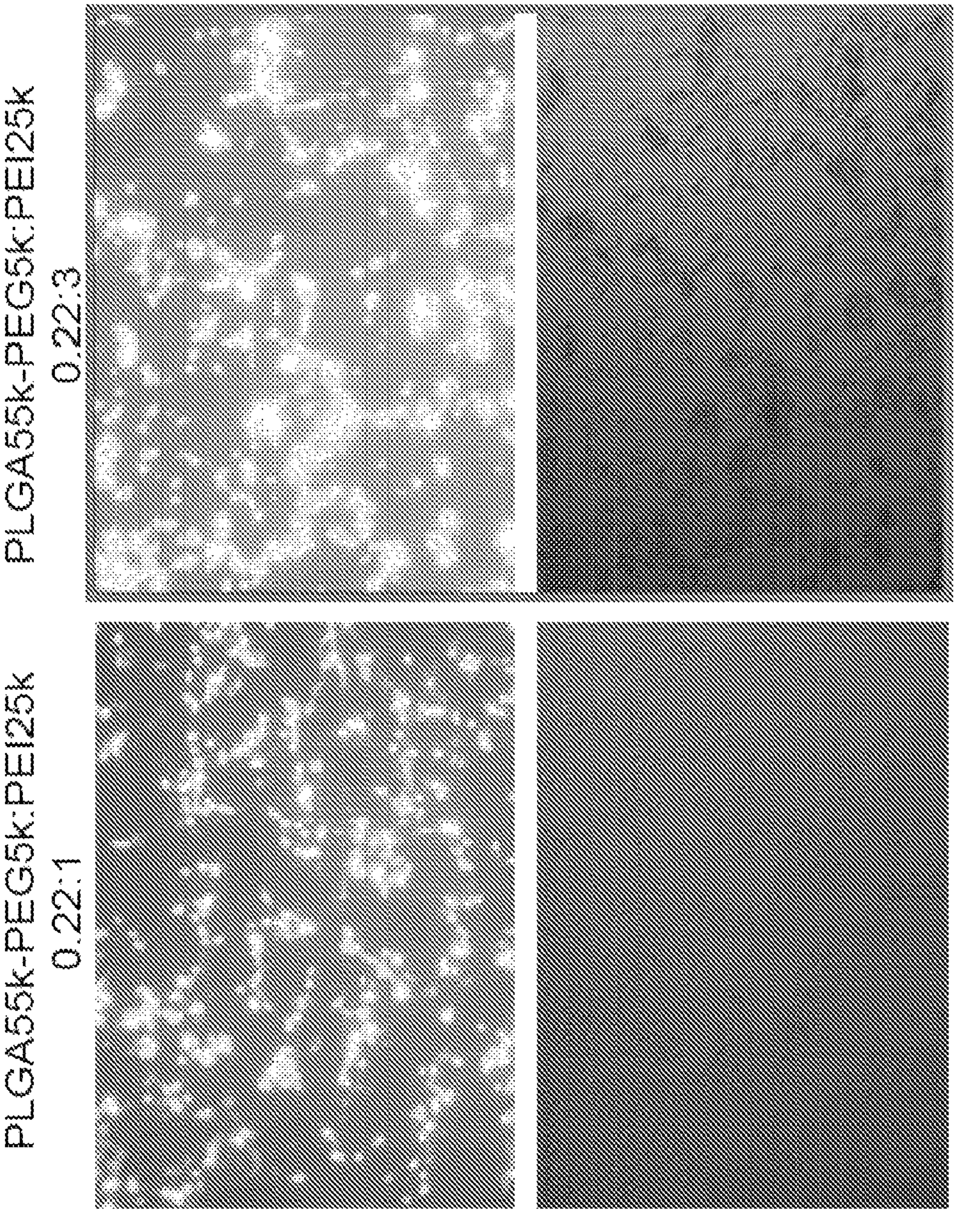

FIG. 12 is a series of fluorescent microscopy images and phase contrast images (black and white) which illustrate the transfection efficiency and toxicity of $PLGA_{55k}$-$PEG_{5k}$/PEI25k nanoparticle delivery of plasmid DNA expressing GFP (green). The ratio of 0.22 mg PLGA-PEG:0.5-1 mg PEI25k gave the best results. Red-framed images indicate highly toxic. PLGA=poly(Lactic Acid-co-Glycolic Acid).

Figure 13:
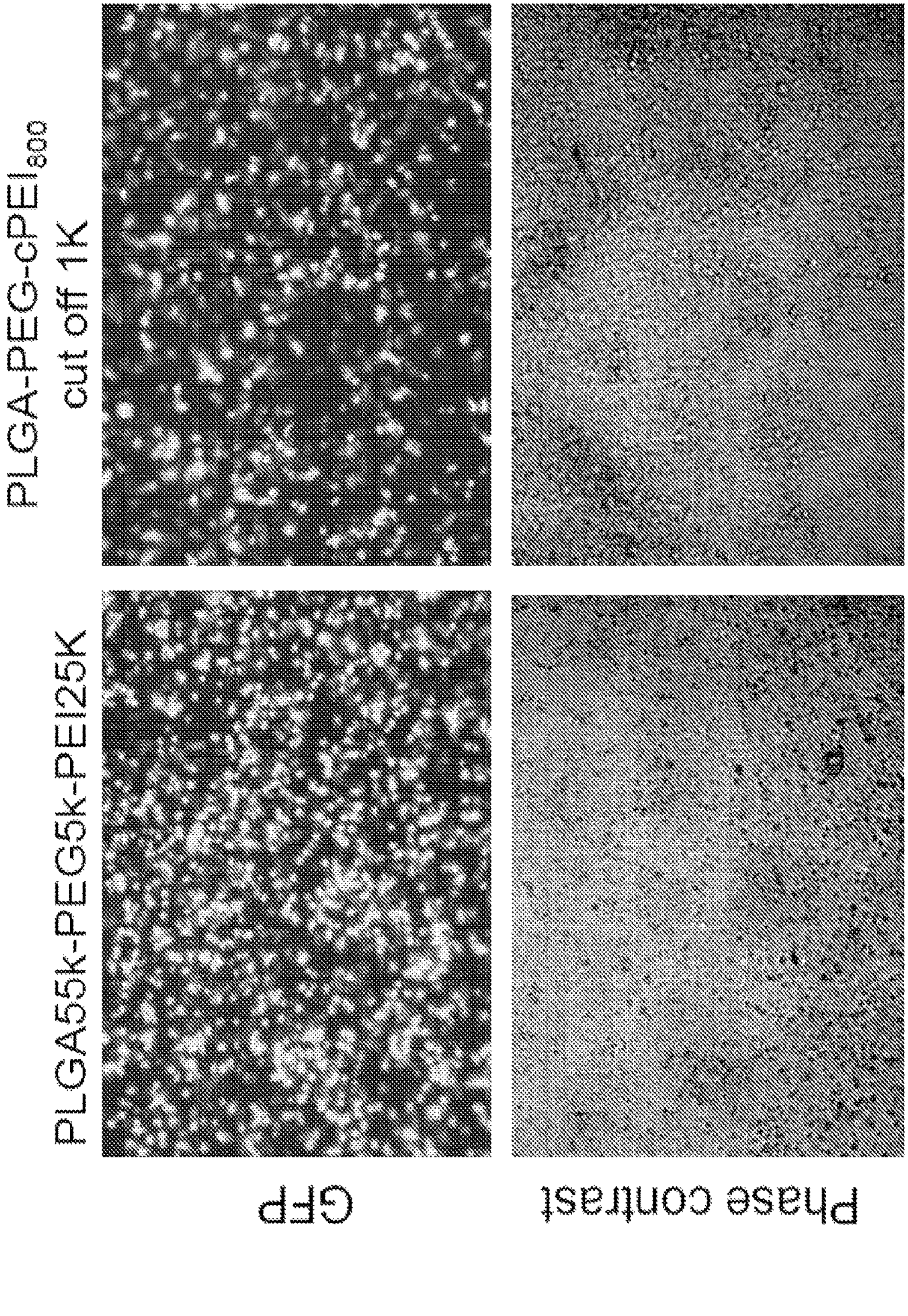
FIG. 13 is a series of fluorescent and phase contrast (black and white) microscopy images which illustrate similar transfection efficiency of $PLGA_{55k}$-$PEG_{5k}$/cPEI800 with 7 k MW cut off nanoparticles and $PLGA_{55k}$-$PEG_{5k}$/PEI25k nanoparticles.
Figure 13:
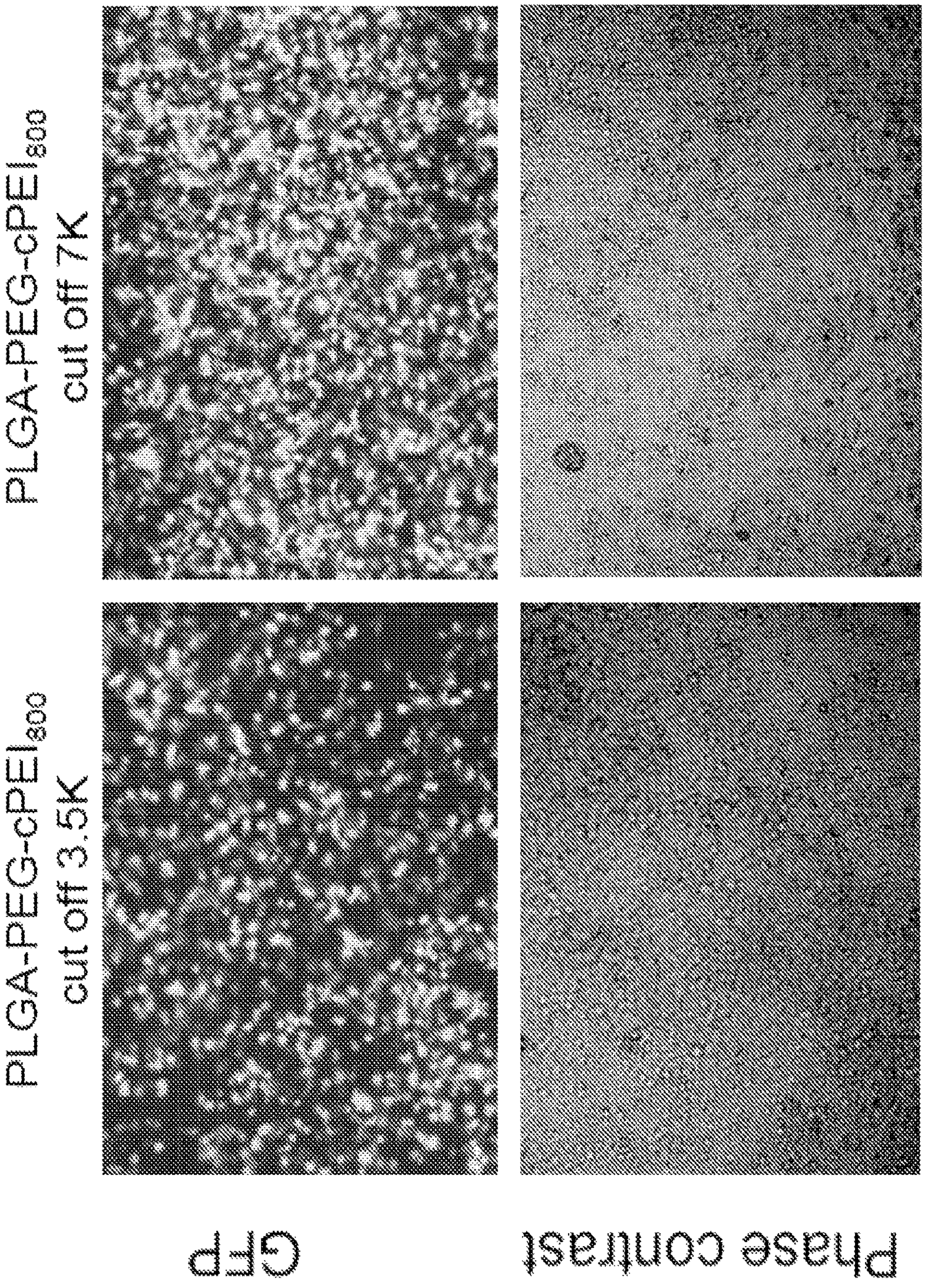

FIG. 13 is a series of fluorescent and phase contrast (black and white) microscopy images which illustrate similar transfection efficiency of $PLGA_{55k}$-$PEG_{5k}$/cPEI800 with 7 k MW cut off nanoparticles and $PLGA_{55k}$-$PEG_{5k}$/$PEI_{25k}$ nanoparticles. cPEI800 with a 1 k or a 3.5 k MW cut off is less effective than cPEI800 with a 7 k MW cut off for transfection. PLGA-PE:PEI=0.22 mg:0.5 mg.

Figure 14:
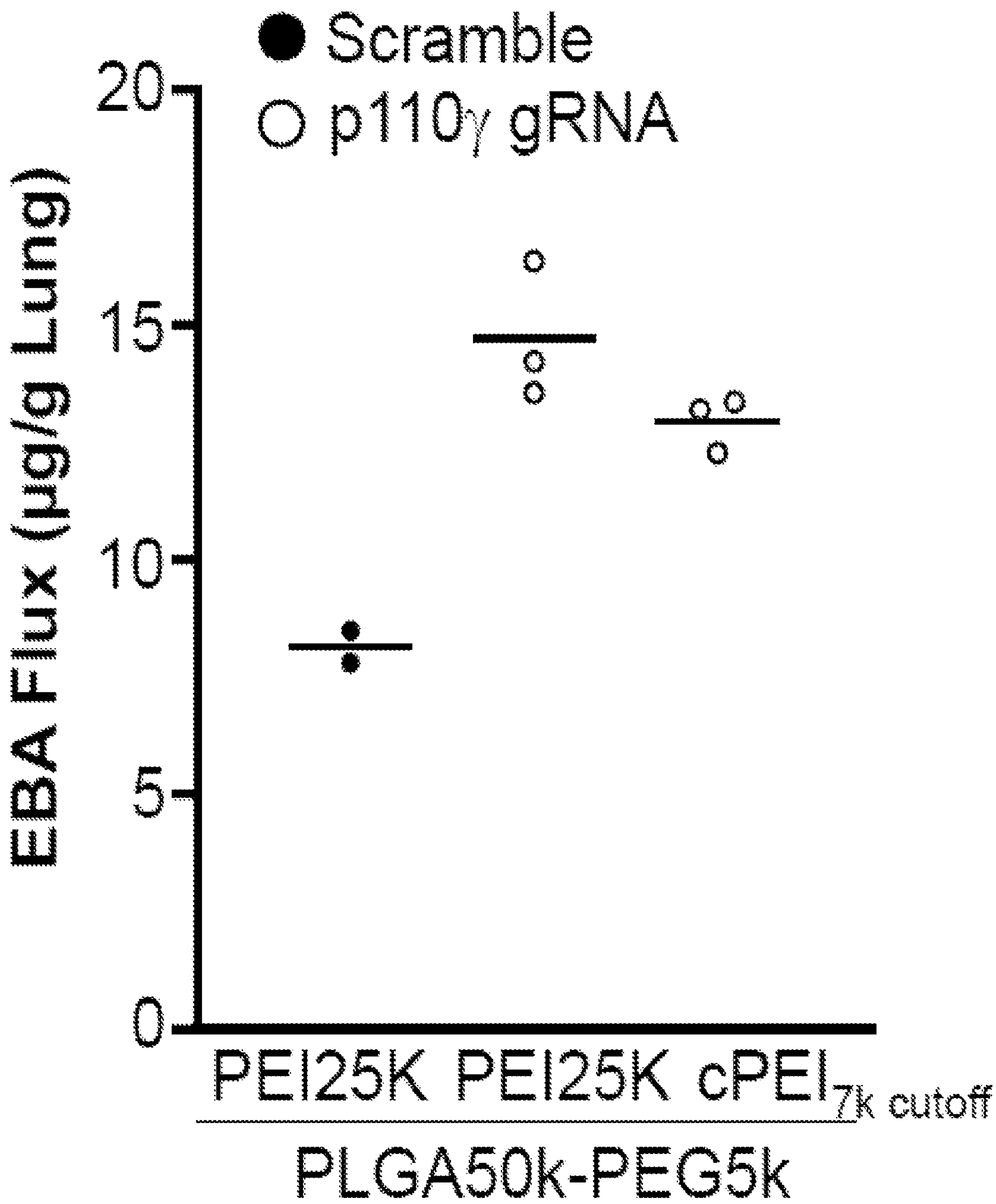
FIG. 14 is a graph which illustrates Evans blue-conjugated albumin extravasation assay showing persistent lung vascular leaking in mice treated with $CRISPR^{CDH5}$ plasmid expressing p110γPI3K gRNA-loaded with PLGA55k-PEG5k/PEI25k or PLGA55k-PEG5k/cPEI (3.5 k cut off) (with similar efficacy) whereas scramble plasmid DNA-treated mice exhibit full recovery at 72 h post-sepsis challenge.

FIG. 14 is a graph which illustrates Evans blue-conjugated albumin (EBA) extravasation assay showing persistent lung vascular leaking in mice treated with $CRISPR^{CDH5}$ plasmid expressing p110γPI3K gRNA-loaded with PLGA55k-PEG5k/PEI25k or PLGA55k-PEG5k/cPEI800 (7 k cutoff) (with similar efficacy) whereas scramble plasmid DNA-treated mice exhibited full recovery at 72 h post-sepsis challenge. Seven days after administration of nanoparticle: DNA, the mice were challenged with lipopolysaccharide (LPS) and lung tissue for collected for EBA assay at 72 h post-LPS. (Note: Published data shows genetic knockout of p110γPI3K impairs vascular repair following lung vascular injury induced by sepsis challenge (Huang et al., *Circulation,* 133: 1093-1103 (2016)).

Figure 15:
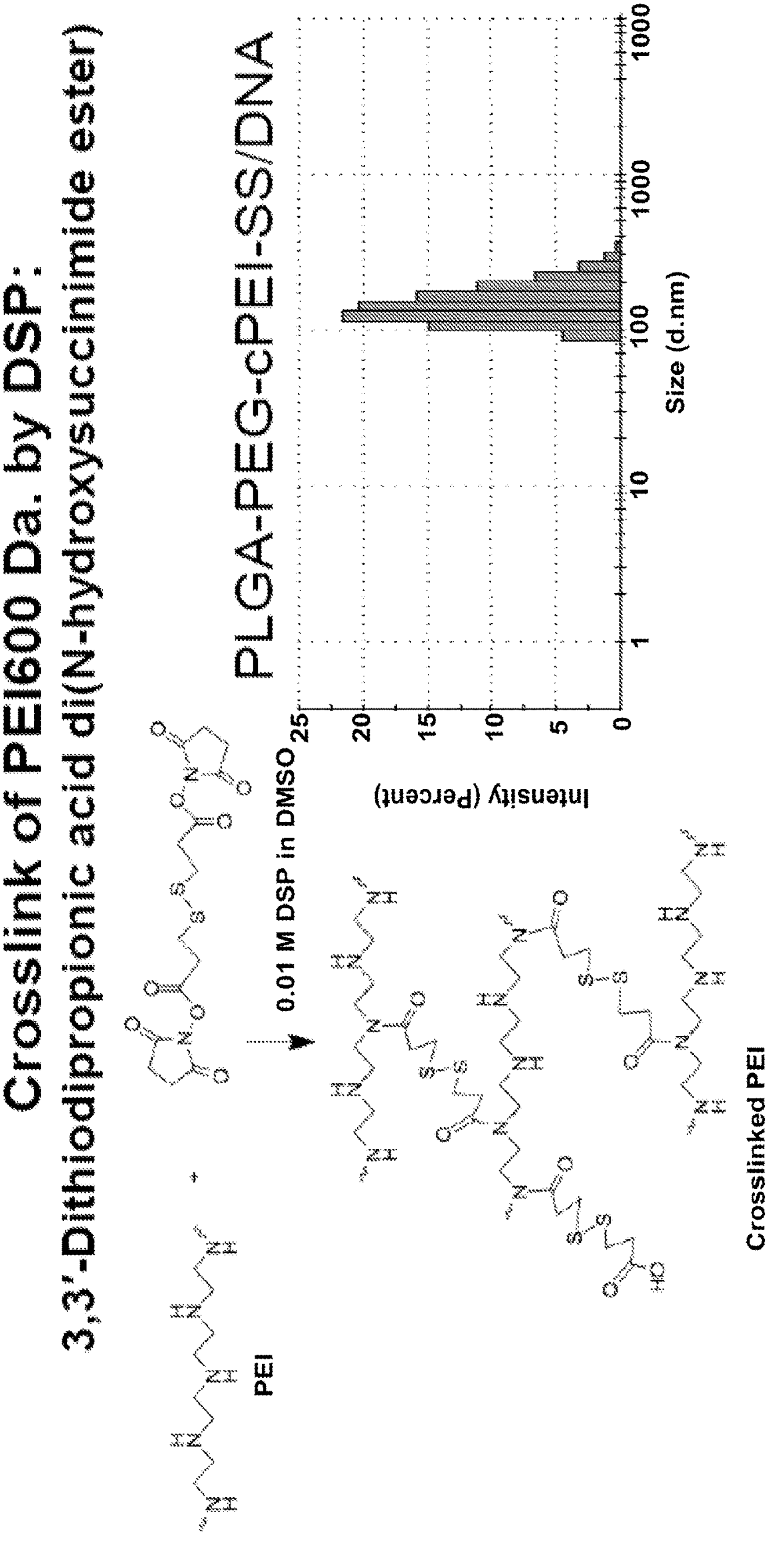
FIG. 15 is a graph which illustrates the procedure of crosslink PEI600 by DSP method and the size distribution of PLGA55k-PEG5k/cPEI-SS/DNA nanoparticle.

FIG. 15 is a graph which illustrates the procedure of crosslink PEI600 by DSP method and the size distribution of PLGA55k-PEG5k/cPEI-SS/DNA nanoparticle.

Figure 16:
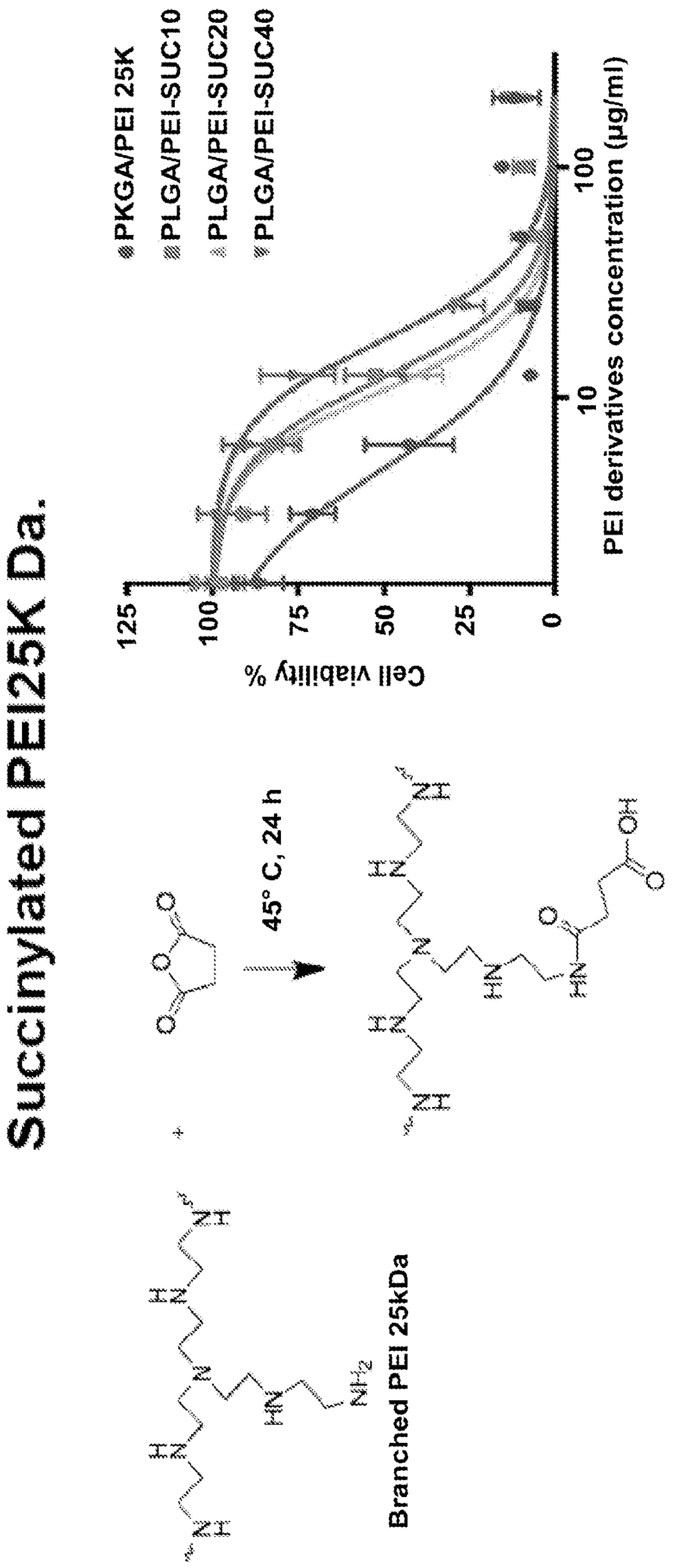
FIG. 16 is a graph which illustrates the procedure of succinylation of PEI25k and cell viability assay showing reduced toxicity of succinylated PEI25k.

FIG. 16 is a graph which illustrates the procedure of succinylation of PEI25k and cell viability assay showing reduced toxicity of succinylated PEI25k.PLGA/PEI25k-SUC40 (40% Succinylation) has the least toxicity.

Figure 17:
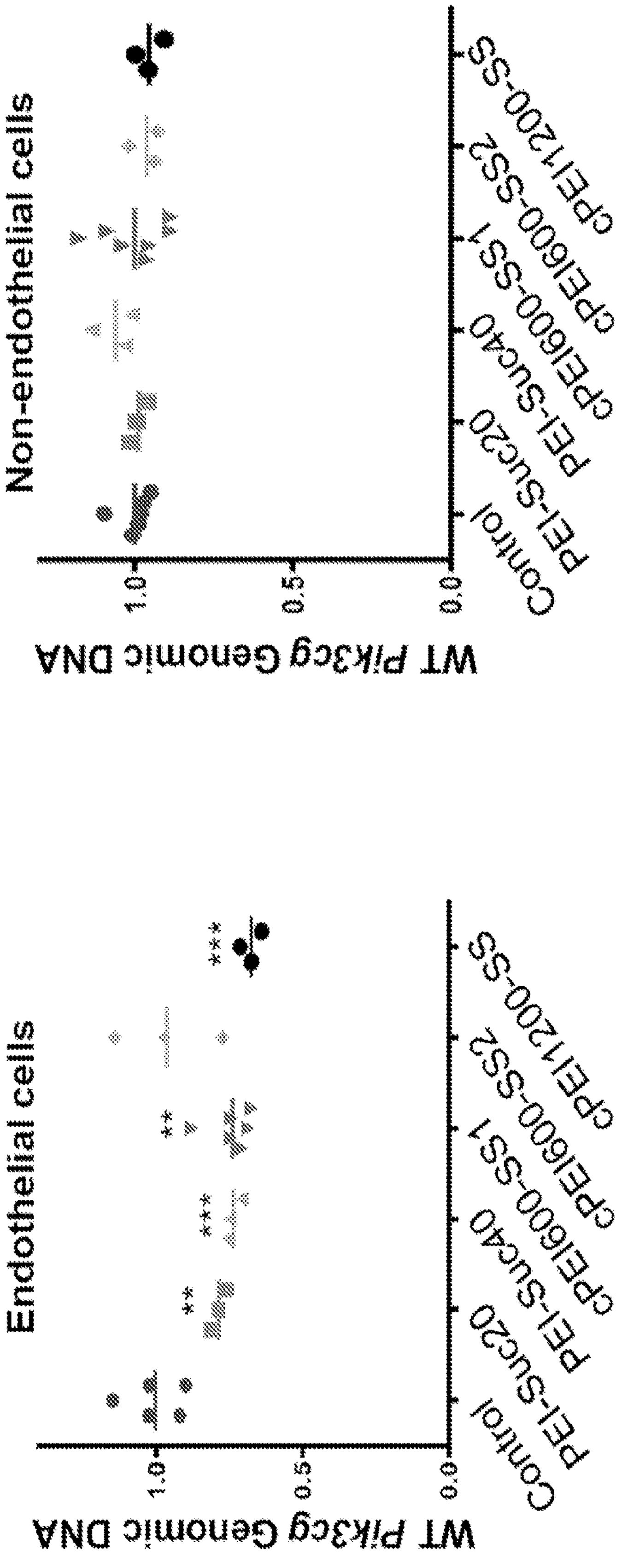
FIG. 17 is a graph which illustrates the genome editing efficiency in lung vascular endothelial cells but not in non-endothelial cells of $CRISPR^{CDH5}$ plasmid expressing p110γPI3K gRNA loaded with PLGA55k-PEG5k/succinylated PEI25k or cPEI600-SS1 or cPEI1200-SS nanoparticles in contrast to cPEI600-SS2 (PEI600:DSP=1:2 molar ratio crosslink reaction condition).

FIG. 17 is a graph which illustrates the genome editing efficiency in lung vascular endothelial cells but not in non-endothelial cells of $CRISPR^{CDH5}$ plasmid expressing p110γPI3K gRNA loaded with PLGA55k-PEG5k/succinylated PEI25k or cPEI600-SS1 or cPEI1200-SS nanoparticles in contrast to cPEI600-SS2 (PEI600:DSP=1:2 molar ratio in the crosslink reaction condition). Lung tissues were collected at 7 days post-nanoparticle:DNAadministration (retroorbitally) for ECs and non-ECs isolation with the anti-CD31 magnetic beads. Genomic DNA were extracted from isolated cells for quantitative PCR analysis. , P<0.01; * P<0.001 versus control.

Example 3—Preparation of PLGA-PEG/PEI600 (low molecular weight PEI) Nanoparticles and Use Thereof for Delivery of DNA In Vivo.

Figure 18:
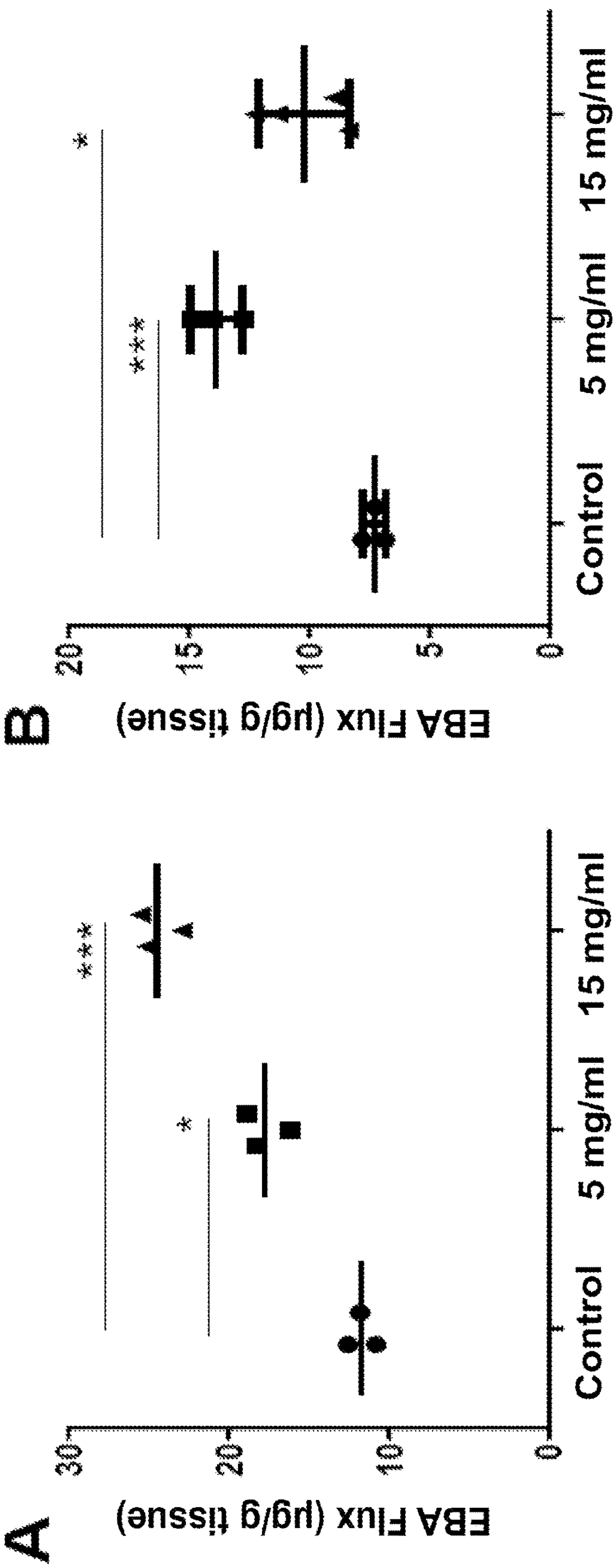
FIG. 18 consists of graphs which illustrate the content of Evans blue-conjugated albumin (EBA) extravasated in mouse lungs at 72 h post-sepsis challenge (A and B). Mice were delivered 30 μg $CRISPR^{CDH5}$ plasmid DNA expressing p110γPI3K gRNA by PLGA55k-PEG5k/PEI600 Da nanoparticles made at a ratio of 0.22 mg/ml/5 or 15 or 40 mg/ml. A graph which illustrates the genome editing efficiency determined by quantitative PCR of wild-type (WT) genomic DNA (C).
Figure 18:
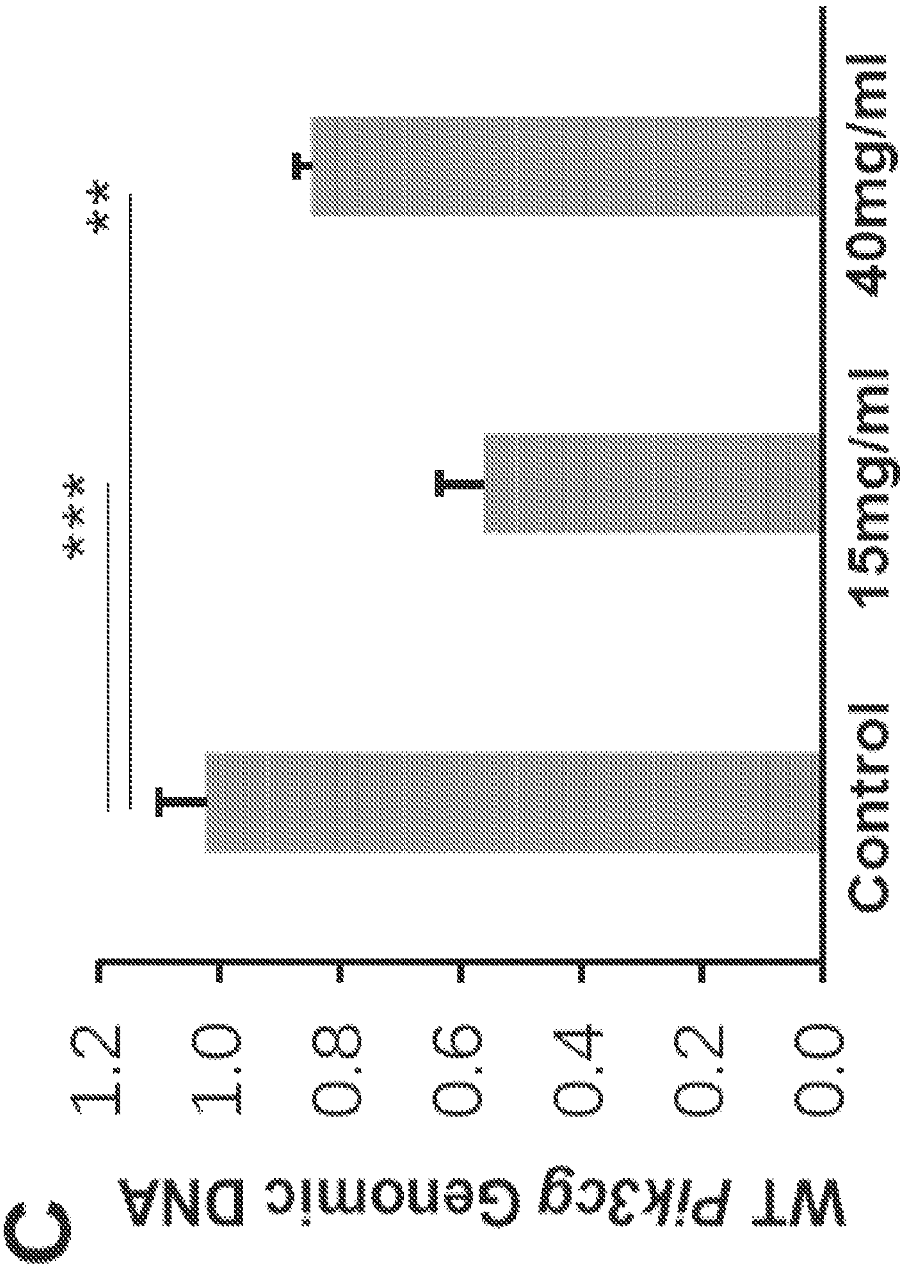

FIGS. 18A and 18B are graphs which illustrate the content of Evans blue-conjugated albumin (EBA) extavasated in mouse lungs at 72 h post-sepsis challenge indicating p110γPI3K gRNA-mediated gene editing impair vascular repair. Mice were delivered 30 μg $CRISPR^{CDH5}$ plasmid DNA expressing p110γPI3K gRNA by PLGA55k-PEG5k/PEI600 Da nanoparticles made at a ratio of 0.22 mg/ml/5 or 15 or 40 mg/ml. FIG. 18C is a graph which illustrates the genome editing efficiency determined by quantitative PCR of wild-type (WT) genomic DNA. , P<0.01; *, P<0.001.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

I claim:

1. A composition comprising:

(a) a nanoparticle comprising a polyethylene glycol (PEG)-b-poly (D,L-lactide) (PLA) (PEG-b-PLA) copolymer coated with a cationic polymer, wherein the PEG-b-PLA copolymer comprises a PLA block having a molecular weight of between about 1,000 Da and about 100,000 Da and a PEG block having a molecular weight of between about 2,000 Da and about 20,000 Da, and (b) one or more cargo molecules associated with the nanoparticle.

2. The composition of claim 1, wherein the cationic polymer is polyethylenimine (PEI), chitosan, poly(2-(dimethylamino)ethyl methacrylate), poly(amino ester)s, dendrimers, polylysines and other poly(amino acids).

3. The composition of claim 1, wherein the one or more cargo molecules are nucleic acid molecules.

4. The composition of claim 3, wherein the one or more nucleic acid molecules is/are DNA.

5. The composition of claim 4, wherein the DNA is in the form of a plasmid, minicircle, or nanoplasmid, and comprises one or more nucleic acid sequences that encodes a gene or a genome editor component.

6. The composition of claim 3, wherein the one or more nucleic acid molecules is/are RNA.

7. The composition of claim 6, wherein the RNA is a small interfering RNA (siRNA), miRNA, long non-coding RNA (lncRNA), antisense RNA, or coding RNA.

8. The composition of claim 1, wherein the one or more cargo molecules are small non-nucleic acid molecules.

9. The composition of claim 1, wherein the cationic polymer is modified or unmodified large molecular weight PEI, wherein the modification is succinylation.

10. The composition of claim 9, wherein the ratio of cargo molecule to PEG-b-PLA copolymer to PEI is about 1 μg:0.5-5 μg:0.5-10 μg.

11. The composition of claim 9, wherein the PEI is PEI25 kDa.

12. The composition of claim 11, wherein the ratio of cargo molecule to PEG-b-PLA copolymer to PEI is 1 μg plasmid DNA:0.5-5 μg PEG-b-PLA copolymer: 1-5 μg PEI25k.

13. The composition of claim 1, wherein the cationic polymer is a modified or unmodified low molecular weight PEI.

14. The composition of claim 13, wherein the modification is acetylation.

15. The composition of claim 13, wherein the ratio of cargo molecule to PEG-b-PLA copolymer to PEI is 1 μg plasmid DNA:0.5-5 μg PEG-b-PLA copolymer: 5-100 μg low molecular weight PEI400, PEI600, PEI800, PEI1200, PEI1800, or PEI2000.

16. The composition of claim 1, wherein the cationic polymer is a modified or unmodified crosslinked low molecular weight PEI polyplex.

17. The composition of claim 16, wherein the crosslinker is a diacrylate, a disulfide, a disimine, a carbamate, an amide, or a ketal.

18. The composition of claim 1, wherein the PEI is diacrylate-crosslinked PEI800 (cPEI800), cPEI400, cPEI600, cPEI1200, cPEI1800, or cPEI2000 optionally wherein the ratio of cargo to PEG-b-PLA copolymer to cPEI is 1 μg plasmid DNA:0.8-5 μg PEG-b-PLA copolymer:1.5-5 μg cPEI800.

19. The composition of claim 1, wherein the PEG-b-PLA copolymer comprises a PLA block having a molecular weight of between about 30,000 Da and about 60,000 Da and a PEG block having a molecular weight of between about 4,000 Da and about 10,000 Da.

20. A method of delivering one or more cargo molecules to a cell, the method comprising contacting the cell with the composition of claim 1, whereby the cargo molecule is delivered to the cell.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1

ttgaaccgta ccacgacagt g                                          21


<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2

accagaacaa gaagtgaccg at                                         22


<210> SEQ ID NO 3
<211> LENGTH: 20
<212> TYPE: DNA
<213> ORGANISM: Artificial Sequence
<220> FEATURE:
<223> OTHER INFORMATION: Synthetic- p110 PI3K gRNA target sequence

<400> SEQUENCE: 3

accgtaccac gacagtgcgc                                            20


<210> SEQ ID NO 4
<211> LENGTH: 20
<212> TYPE: DNA
<213> ORGANISM: Artificial Sequence
<220> FEATURE:
<223> OTHER INFORMATION: Synthetic- Vegfr2 gRNA target sequence

<400> SEQUENCE: 4

caacccttca gattacttgc                                            20
```